United States Patent [19]
Whitener

[11] Patent Number: 4,897,597
[45] Date of Patent: Jan. 30, 1990

[54] APPARATUS AND METHODS FOR DETECTING WET AND ICY CONDITIONS

[75] Inventor: Miles B. Whitener, St. Louis, Mo.

[73] Assignee: Surface Systems, Inc., St. Louis, Mo.

[21] Appl. No.: 281,822

[22] Filed: Dec. 8, 1988

[51] Int. Cl.$^4$ .............................................. G01R 27/02
[52] U.S. Cl. .................................. 324/693; 73/336.5; 324/700; 340/580
[58] Field of Search .................. 324/61 P, 65 P, 61 R, 324/65 R, 65 CR; 340/580, 581, 602; 244/134 F; 73/336.5, 170 R, 335, 336

[56] References Cited

U.S. PATENT DOCUMENTS

| | | | |
|---|---|---|---|
| 3,243,793 | 3/1966 | Goldman | 340/580 |
| 3,255,412 | 6/1966 | Liu | 324/61 |
| 3,320,946 | 5/1967 | Dethloff et al. | 128/2.1 |
| 3,582,728 | 6/1971 | Thoma | 317/246 |
| 3,613,063 | 10/1971 | Ciemochowski | 340/234 |
| 3,636,444 | 1/1972 | Strawn et al. | 324/61 R |
| 3,855,861 | 12/1974 | Zimmermann et al. | 73/304 R |
| 3,873,927 | 3/1975 | Overall | 328/4 |
| 3,882,381 | 5/1975 | Gregory | 324/61 R |
| 3,974,993 | 8/1976 | Hammecke | 246/428 |
| 3,986,110 | 10/1976 | Overall et al. | 324/61 R |
| 4,135,151 | 1/1979 | Rogers et al. | 324/61 R |
| 4,164,868 | 8/1979 | Suntola | 73/336.5 |
| 4,210,021 | 7/1980 | Vykhodtsev et al. | 340/580 X |
| 4,222,044 | 9/1980 | Boschung | 340/581 |
| 4,281,286 | 7/1981 | Briggs | 324/61 R |
| 4,335,613 | 6/1982 | Luukkala | 73/599 |
| 4,383,770 | 5/1983 | Boschung et al. | 374/25 |
| 4,500,940 | 2/1985 | Kuisma et al. | 361/286 |
| 4,523,142 | 6/1985 | Murata et al. | 324/65 R |
| 4,679,160 | 7/1987 | Whitener | 364/563 |
| 4,765,187 | 8/1988 | Weinstein | 73/304 R |
| 4,766,369 | 8/1988 | Weinstein | 324/61 R |
| 4,801,865 | 1/1989 | Miller et al. | 73/336.5 X |

FOREIGN PATENT DOCUMENTS 2078982 11/1971 France .
2180350 A 3/1987 United Kingdom .

OTHER PUBLICATIONS

"Aquaplaning Risk on Runways is Measured", Airport Services Management, 11/70, p. 31.
J. E. Forbat, "An Operational aid for warning of aquaplaning conditions" Interavia Aviation, Astronautics, Electronics, No. 2, 1971, 4 pgs.
"Winter Beware", brochure of Surface Systems, Inc., 1980, 4 pp.
Matthews et al., The Development of Ice Detection Techniques, Cranfield Institute of Technology, face sheets, pp. 1–8, 6 pgs. of drawings, undated.
"Winter Beware: Scan® System 16 TM is watching you!", brochure of Surface Systems, Inc., 1981, 4 pgs.
Road Weather System, Vaisala, part 1983, part 1986, face sheet, pp. 1(13)–13(13), 1(8)–8(8), 2 pgs. specif., pp. 1(5)–5(5), 2 pgs. dwgs., pp. 1(2)–2(2), Appendix D.
Kelly et al., "SCAN provides data for ice/snow control and forecasting", ICAO Bulletin, Apr. 1987, 4 pgs.

Primary Examiner—Reinhard J. Eisenzopf
Assistant Examiner—Robert W. Mueller
Attorney, Agent, or Firm—Senniger, Powers, Leavitt and Roedel

[57] ABSTRACT

Apparatus that detects the presence and condition of precipitation on the surface of a pathway. The apparatus has a block of electrically insulative material adapted to be embedded in the pathway with a top surface exposed to precipitation. A sensor is embedded in the block for sensing a physical property of the precipitation to produce a sensor output which is also influenced by a depth of the precipitation. Part of the top surface of the block has a well that is generally curved in outline above the sensor for gathering precipitation for the sensor. Advantageously, the influence of precipitation depth on the sensor is diminished. Other apparatus and methods are also disclosed.

45 Claims, 11 Drawing Sheets

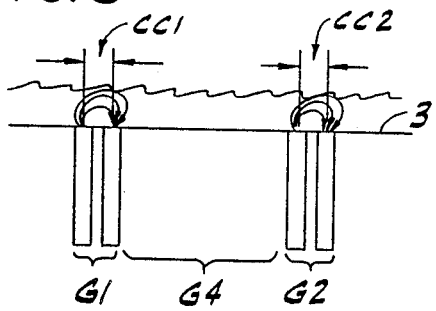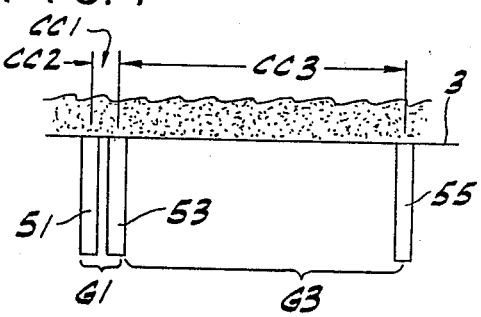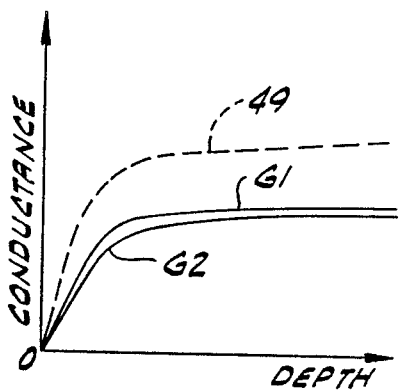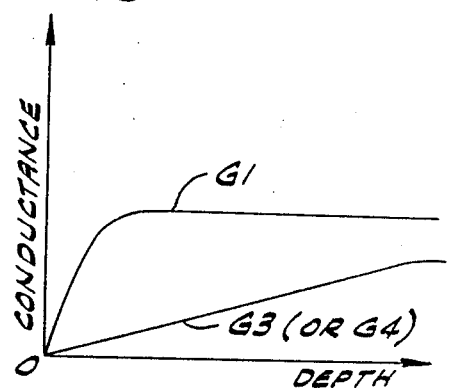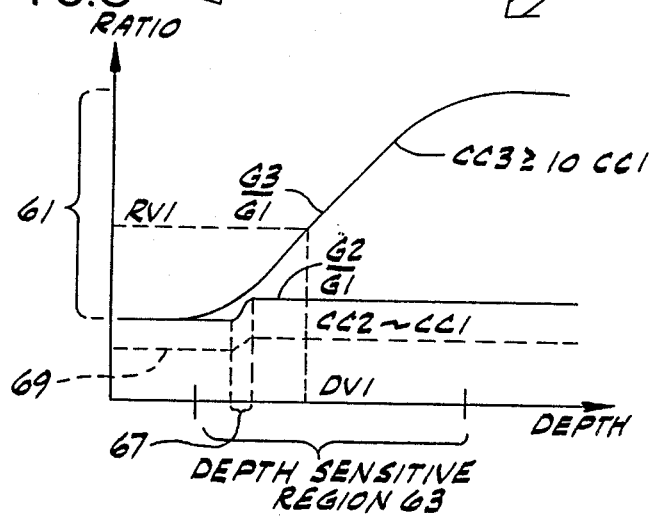

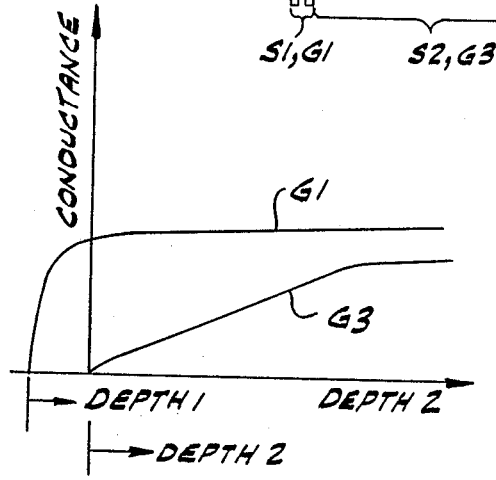
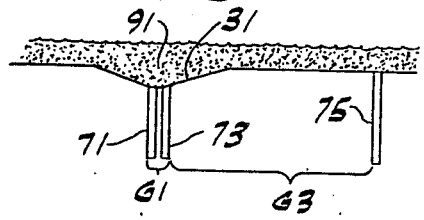
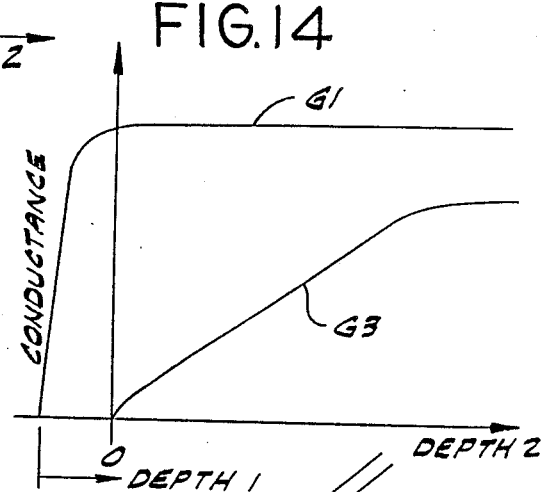
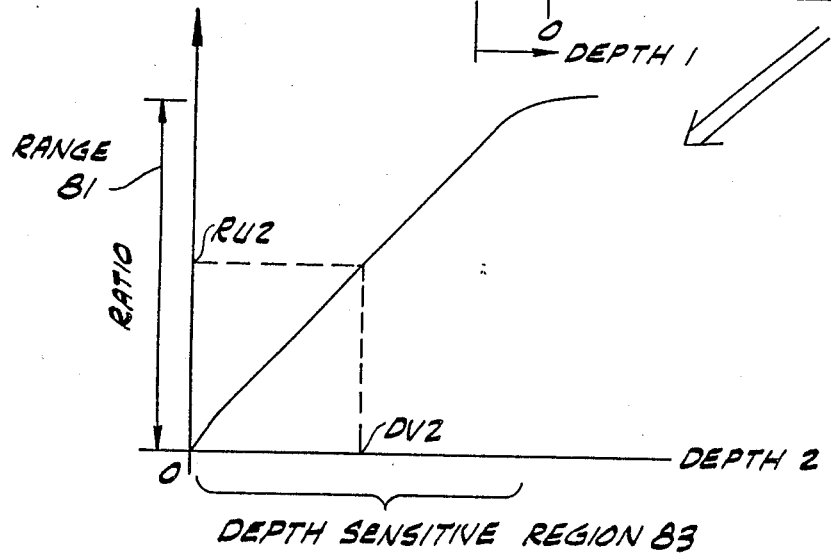

APPARATUS AND METHODS FOR DETECTING WET AND ICY CONDITIONS

NOTICE

Copyright © 1988 Surface Systems, Inc. A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

The present invention relates to apparatus and methods for detecting wet or icy conditions due to precipitation accumulating on a surface of a pathway, such as a highway, a bridge, an airport runway, or a building floor. More particularly, the present invention relates to precipitation sensing apparatus which can be embedded in a pathway for sensing the presence, type or amount of atmospheric precipitation and methods of its manufacture and operation.

Apparatus which detects wet and icy surface conditions is a potentially indispensable aid to motorists, highway departments, airport managers, pilots and others. A motorist can be made aware of an icy condition on a bridge deck before crossing it and take the necessary precautions. Likewise, once an airport manager is aware of a slippery or icy condition on one or more of the airport runways, planes can be diverted to a non-icy runway and deicing procedures initiated on the affected runways. Motorists can be warned of a light accumulation of water on a dirty highway, which is a hazard almost as well known as it is difficult to see.

When an aircraft lands on a runway covered with water, a condition called hydroplaning can cause a dangerous skid. The minimum depth of water at which hydroplaning first occurs is inversely related to the landing speed of the aircraft, generally speaking. Airport management faces a safety dilemma since aircraft cannot be allowed to land on runways which are unsafe for them. However, unnecessary closing of runways must be avoided to prevent congestion of the available airspace and consequent reduction of safety in the air. Consequently, only those runways should be closed which are actually hazardous to the particular aircraft requesting clearance to land. Accurate precipitation depth information over a wide range of depths is essential to safety-related decisions, and warning information is also needed as soon as there is incipient icing of a wet pathway.

In coassigned U.S. Pat. No. 4,135,151, precipitation on the sensor is identified as water, slush, or ice by a capacitance and conductance approach. In coassigned U.S. Pat. No. 4,281,286 at least two different frequencies are used in a capacitance and conductance approach, depending on whether impurities are or are not present in the precipitation. Both of these patents U.S. Pat. Nos. 4,135,151 and 4,281,286 are specifically incorporated herein by reference.

French patent No. 2078982 suggests an assembly with a capacitance and resistance approach. The resistance sensor has concentric electrodes. When deicing agents are present on the ground, these modify the conductivity of the surface water and in order to compensate this effect the resistance between two other concentric electrodes comparable in dimensions to the electrodes of the resistance sensor is used as a reference to correct a depth signal.

U.S. Pat. No. 3,613,063 shows two concentric metal electrodes separated by an air gap for entry of precipitation. The outer metal electrode has a dished, concave shape in one version.

U.S. Pat. No. 4,335,613 shows an elongated ultrasonic sensor placed in a groove in a road surface.

Gaps and grooves present self-evident problems of dirt retention and the need for frequent maintenance. Moreover, devices with gaps or grooves are susceptible to damage by repeated freezing and thawing cycles in harsh environments and also by tire impact and wear. Compensation for impurities by multiple electrodes of comparable dimensions results in a restricted range of depth measurement.

Also, conductance-based sensors continue to be subject to mingled effects of both precipitation depth and impurities on measured conductivity. This mingling of effects presents a problem of determining and isolating the contributions made by precipitation depth and impurity concentrations respectively. Moreover, impurity concentration can vary markedly over even relatively short distances, casting a cloud of uncertainty on the prior multiple electrode approaches. Chemical reactions on sensor electrodes exposed to the elements causes dielectric deposits that further complicate the measurement problem. Evaporation of a wet surface may result in a very thin precipitation layer that has very low conductance but is still detectable by a capacitance sensor, complicating the determination of precipitation type.

The ultrasonic measurement approach of coassigned U.S. Pat. Nos. 4,769,160 and 4,750,117 offers an attractive alternative technology in depth sensing. However, it is desired to make further improvements in conductance sensors so that these also are utilized to their full potential for accurate characterization of precipitation, for detecting impurities and depth sensing as well.

SUMMARY OF THE INVENTION

Among the objects of the present invention are to provide improved apparatus and methods of detecting wet and icy conditions which more effectively isolate the effect of impurities on measured conductivity from the influence of precipitation depth thereon; to provide improved apparatus and methods of detecting wet and icy conditions which provide a markedly enhanced range of depth over which depth measurement can be more accurately determined; to provide improved apparatus and methods of detecting wet and icy conditions which provide increased accuracy of conductance-based depth measurement in relatively thin layers of precipitation; to provide improved apparatus and methods of detecting wet and icy conditions when a surface is almost dry; to provide improved apparatus and methods of detecting wet and icy conditions which detect excessive dielectric buildup on exposed electrodes due to corrosion effects; to provide improved apparatus and methods of detecting wet and icy conditions which provide improved accuracy of conductance based depth measurement in layers which have impurity concentrations that vary greatly over the surface of the pathway; to provide more economical and reliable methods of constructing and operating apparatus for detecting wet and icy conditions; and to provide improved apparatus for detecting wet and icy conditions which is durable, economical and reliable even in demanding and harsh environments.

Generally, one form of the invention is an apparatus that detects the presence and condition of precipitation on the surface of a pathway. The apparatus has a block of electrically insulative material adapted to be embedded in the pathway with a top surface exposed to precipitation. A sensor is embedded in the block for sensing a physical property of the precipitation to produce a sensor output which is also influenced by a depth of the precipitation. Part of the top surface of the insulative block itself has a well that is generally curved in outline above the sensor for gathering precipitation for the sensor. Advantageously, the influence of precipitation depth on the sensor is diminished.

Generally, another form of the invention is an apparatus for detecting the presence and condition of precipitation on the surface of a pathway. The apparatus has a block of electrically insulative material adapted to be embedded in the pathway with a top surface exposed to precipitation. The apparatus also includes a sensor having at least three electrical conductors terminating substantially flush with the top surface of the block. The conductors have portions that are exposed to the precipitation. A first distance separates the exposed portions of two of the electrical conductors and a second distance separates the exposed portions of a particular pair of the electrical conductors, and the second distance is at least ten times the first distance. Circuitry connected to the electrical conductors measures a first quantity related to electrical conductance between the two electrical conductors that are separated by the first distance and a second quantity related to electrical conductance between the particular pair of conductors that are separated by the second distance which is at least ten times the first distance, and generates an output signal indicative of precipitation condition as a joint function of the first and second quantities.

Generally, a further form of the invention is an apparatus for detecting the presence and condition of precipitation on the surface of a pathway, that has a block of electrically insulative material adapted to be embedded in the pathway and exposed to precipitation. Included is a sensor that has at least two electrical conductors affixed to the block and exposed to the precipitation. Corrosion forms on the conductors and endows them with a series capacitance in the presence of precipitation. Circuitry produces a warning when the series capacitance in the presence of precipitation is less than a predetermined capacitance.

Other apparatus and methods are also described and claimed herein, and other objects and features will be in part apparent and in part pointed out hereinafter.

BRIEF DESCRIPTION OF THE DRAWINGS

FIG. 5 is a cross-sectional view of conductors embedded in a block for conductance sensing;

FIG. 6 is a graph of electrical conductance versus depth of precipitation for two pairs of conductors of FIG. 5;

FIG. 7 is a cross-sectional view of three conductors embedded in a block for conductance sensing according to the invention;

FIG. 8 is a graph of electrical conductance versus depth of precipitation for two pairs of the three conductors of FIG. 7;

FIG. 9 is a graph of ratio of electrical conductances versus depth of precipitation, with one ratio curve (G2/G1) derived from conductances in FIG. 6 and another, more advantageous, ratio curve (G3/G1) derived from conductances in FIG. 9;

FIG. 10 is a cross-sectional view of the inventive apparatus of FIGS. 1 and 2 with three conductors embedded in a block for conductance sensing and having a precipitation-gathering well over two of the conductors;

FIG. 11 is a grpah of electrical conductance versus depth of precipitation for two pairs of conductors of FIG. 10;

FIG. 12 is a graph of a ratio of the electrical conductance curves of FIG. 11 versus depth of precipitation, which ratio in the inventive apparatus of FIG. 1 is essentially independent of impurity concentration;

FIG. 13 is a cross-sectional view corresponding to FIG. 10 showing conductance sensing when there is substantial concentration of deicer in the precipitation;

FIG. 14 is a graph of electrical conductance versus depth of precipitation for two pairs of conductors of FIG. 13 in the presence of substantial concentration of deicer in the precipitation wherein their conductance ratio is also represented by FIG. 12;

Corresponding reference characters indicate corresponding parts throughout the several views of the drawings.

DETAILED DESCRIPTION OF THE PREFERRED EMBODIMENTS

Figure 1:
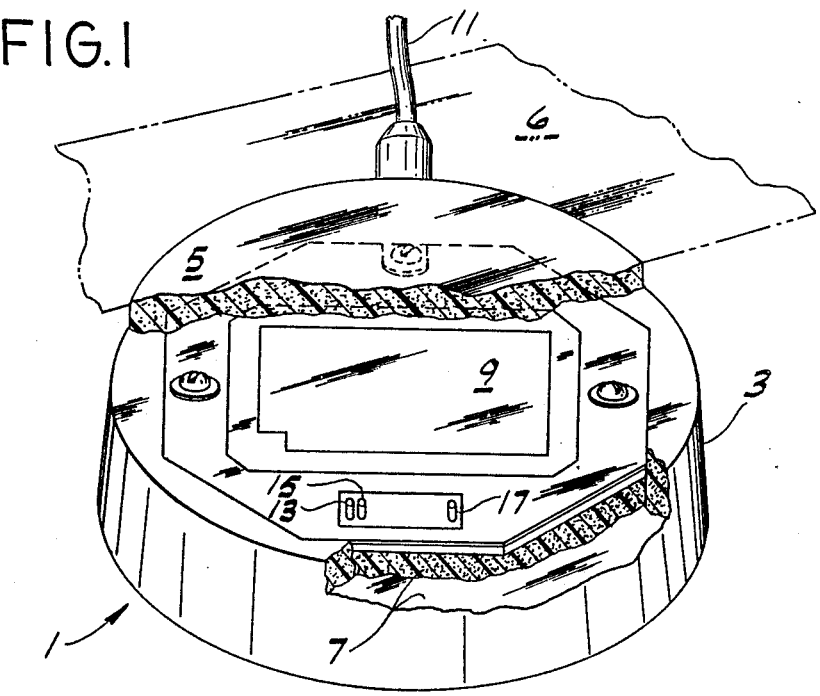
FIG. 1 is pictorial view, partially cut away, of apparatus of the invention embedded in a pathway.

A preferred embodiment of an apparatus 1 of the present invention is indicated generally in FIG. 1. Apparatus 1 detects the presence and condition of precipitation on the surface of a pathway 6. Apparatus 1 has a block 3 of electrically insulative material having a top surface 5. Block 3 is a durable molded piece adapted to be embedded in pathway 6 with the top surface 5 of the block 3 substantially flush with the surface of the pathway 6. In this way top surface 5 is exposed to atmospheric precipitation, such as rain, sleet, and snow and water freezing to ice on the pathway. Top surface 5 is also exposed to any impurities such as salt, calcium chloride, or other deicers which may be present on the pathway. The electrically insulative material making up block 3 includes a thermosetting synthetic resin material 7 having a dielectric constant which is relatively independent of temperature.

A large, generally rectangular capacitive sensor electrode 9 is encapsulated in block 3 beneath top surface 5 of block 3 and connected to electronic circuitry in block 3, as described in detail in coassigned U.S. Pat. Nos. 4,281,286 and 4,135,151 both of which are incorporated herein by reference. Electrode 9 and the circuitry which utilizes it are an example of a means surrounded by the block for independently capacitively sensing the presence of precipitation and means connected thereto for producing a first electrical signal indicative of presence of precipitation. An electrical cable 11 connects the circuitry in the block 3 to a computer described later herein.

In FIG. 1, the top surface 5 is diagrammatically cut away to show three important conductivity measuring electrodes including electrical conductor 13, 15 and 17, which are illustrated as tiny pins or rods. Electrical conductors 13 and 15 are closely spaced while electrical conductor 17 lies at a substantially greater distance from the other two. Improved accuracy and a substantially wider range of depths can be measured by a conductance-based process using these conductors 13, 15 and 17. Electrical measurements are made over first and second distances through the precipitation where the second distance is at least ten times the first distance.

Figure 2:
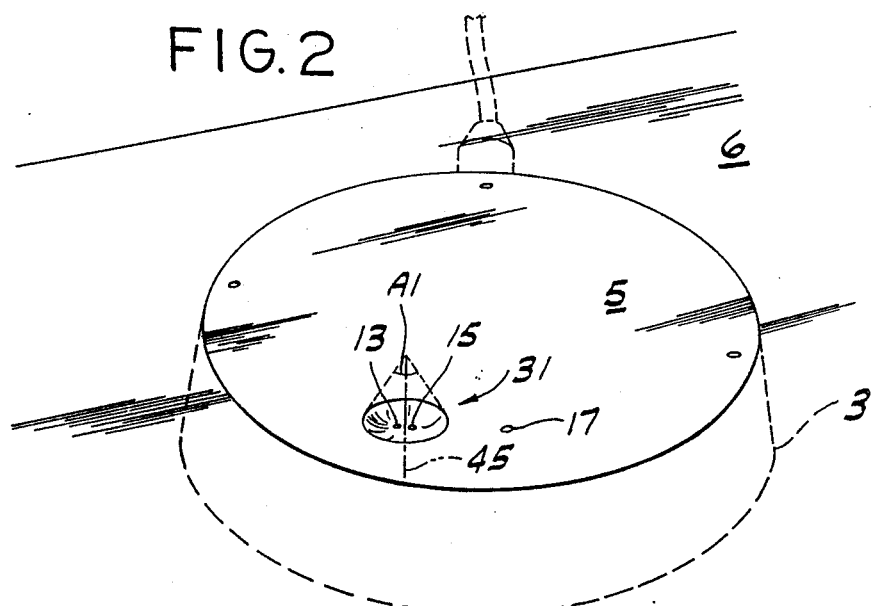
FIG. 2 is perspective view of the apparatus of FIG. 1 with a well for inventively gathering precipitation around sensor conductors.

In FIG. 2, the block 3 is embedded substantially flush with the pathway 6 and visually blends with the pathway 6 so as to be virtually indistinguishable from the pathway. The electrical conductors 13 and 15 act as a sensor embedded in and thereby affixed to the block 3 for sensing a physical property of the precipitation such as its conductivity to produce a sensor output which is also influenced by a depth of the precipitation.

Figure 3:
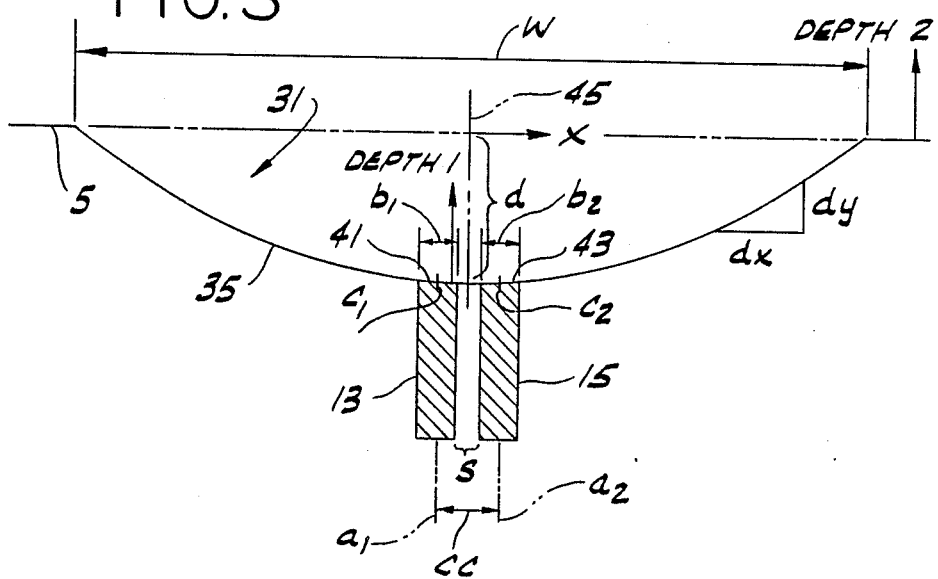
FIG. 3 is an enlarged cross-sectional view of the well and two conductors of FIG. 2.

In FIGS. 2 and 3 the top surface 5 of the block 3 is further improved with smoothly curved well 31 that is generally curved in outline above the electrical conductors 13 and 15. Well 31 gathers precipitation for the electrical conductors 13 and 15, thereby diminishing the influence of precipitation depth on conductance measurements made by them. The well 31 is generally round with a circular outline in FIG. 2. Well 31 is formed in the synthetic resin material as a radially symmetric depression, having a cross-section shaped like an arc of a circle in one embodiment.

Various oval or other rounded outlines (in plan view) for well 31 are usable. Also, a variety of cross-sectional shapes can be used. The well 31 can have an outline or boundary that intersects the rest of the top surface 5 in a distinct edge, shoulder, rim or brim. The boundary can alternatively be a fringe that curves into the rest of the top surface with no distinct edge.

The well 31 provides a remarkable precipitation-depth-amplifying and fluidic storage function that markedly improves the depth sensing and conductivity measuring capabilities of this embodiment. Meniscus effects are reduced due to microscopic roughening of the surface 5 including well 31 by sustained exposure to sunlight.

The electrical conductors 13 and 15 are embedded in block 3 substantially flush with a curved surface 35 of the well 31 in FIG. 3. Precipitation in well 31 has a precipitation depth DEPTH1 measured vertically from the deepest point. The depth of the well 31 is d, and when the precipitation fills well 31, DEPTH1 equals d.

In discussing the properties of the well 31, a concept of depth amplification factor A is introduced. The depth amplification factor of a well for the present purposes is regarded as a factor equal to depth d divided by a depth or accumulation DEPTH2 of precipitation (as measured on a flat surface) that fills the well 31 full. Surface tension effects and spilling of precipitation from the rest of surface 5 laterally into the well 31 are ignored. Therefore, the concept of depth amplification factor provides a numerical lower bound based on geometric considerations for describing the effectiveness of the well 31 in gathering precipitation for the sensor beneath it.

For example if 2 millimeters accumulation of precipitation is sufficient to fully fill a well that is 3 millimeters deep, then the depth amplification factor of the well is 3 divided by 2, or 1.5. A well with vertical walls has a depth amplification factor of unity, since lateral inward spillage is ignored. A depth amplification factor of 1.71 is provided by a well with a flat bottom and a radially symmetric 45 degree inclined conical side surface (not shown) which meets the bottom at a radius equal to the well depth. For the present purposes, any well with a depth amplification factor of 1.5 or more is particularly advantageous for gathering precipitation around a sensor, since the well begins to fill rapidly as soon as even a small amount of precipitation enters. In this way, the well is effective for use with any sensor of a physical property or characteristic or constant of the precipitation. The sensor can be based on conductance, ultrasonics, microwaves, capacitance or any other effective principle in alternative embodiments.

Well 31 preferably satisfies one or more of the following conditions. The well should be relatively avoidant to dirt collection. If dirt does collect, wind and water should remove the dirt readily. The well should be as deep as possible to suppress wind-generated waves on the surface of water gathered or collected by the well. The well should not be so large that the size of block 3 needs to be increased. The well should not be so small that meniscus and surface tension considerations become significant or pin spacing becomes impractically small. The well should be smooth and curved, thereby substantially inhibiting deterioration of the well when water therein freezes to ice. And, as discussed above, the well should rapidly fill when even a small amount of precipitation occurs so that conductivity measurements can be made in relatively controlled conditions in the field.

These conditions are generally satisfied by a well that is geometrically specified by one or more of the following ranges and considerations. The well preferably has a width W (FIG. 3) that is between 3 and 12 times the well depth, and even more preferably has a width W that is between 3 and 5 times the well depth. If the well is oval, its major and minor width dimensions preferably both lie in the range.

Figure 4:
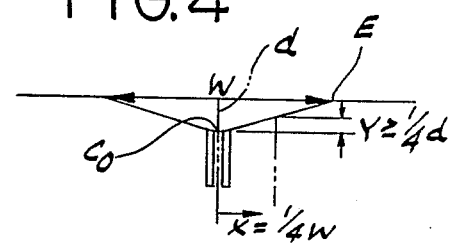
FIG. 4 is a cross-sectional view of a well having an alternative shape for use in the practice of the invention.

The well 31 has a cross-section in FIG. 3 that has a maximum slope dy/dx which is between 0.5 and 2.0 in magnitude. The depth amplification factor preferably exceeds 1.5 and even more preferably 2.0. In another preferred dimensional relationship illustrated in FIG. 4, the well slopes smoothly from the center Co to an edge E of the well so that the surface of the well rises by an amount y at least one-fourth (¼) the well depth d at a distance X of no more than one-fourth (¼) the widest well width dimension W.

Figure 3A:
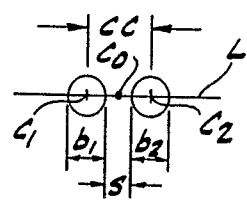
FIG. 3A is a plan view of exposed portions of the conductors in the well in FIG. 2.

In a further dimensional consideration, the pair of conductors 13 and 15 in FIG. 3 have exposed portions 41 and 43 thereof exposed to precipitation gathered by the well 31 when precipitation occurs. The exposed portions 41 and 43 have a center-to-center spacing CC, and the well has its depth d at least twice the spacing CC. In FIGS. 3 and 3A, the exposed portions have respective centers c1 and c2 and respective breadths b1 and b2 along a line L between the centers. Breadths b1 and b2 are each less than the center-to-center spacing CC. A desirable geometric balance is obtained when each of the breadths b1 and b2 is less than the center-to-center spacing CC, and in some embodiments the breadths are equal and are each about two-thirds (⅔) of the spacing CC.

The exposed portions 41 and 43 are also separated by a separation distance s which is less than one-half the well depth d. Distance s between exposed portions of conductors in the present embodiment is regarded as the length of the shortest line segment along the surface of the block between the exposed portions. The breadth of a circular portion is its diameter. The center of an exposed portion of conductor is regarded as the center of a circle if the conductor has circular cross-section. However, if a conductor has an exposed portion of another shape, the center is for present purposes is the centroid of the geometric shape of the exposed portion. If the conductors are parallel rods or pins, the center-to-center spacing is the same as the distance between axes a1 and a2 of the rods or pins. However, the rods or pins may have axes that are oblique or skewed, or there may be no axes at all. Accordingly, the center-to-center spacing CC for the present purposes is the length of the line segment joining the centers of exposed portions of conductors.

In one example, a well 31 of circular outline has a 25.4 millimeters (1 inch) diameter and a well depth of 3.2 millimeters (0.125 inch). Conductor pins 13 and 15 have a diameter (breadth) of 0.89 millimeter (0.035 inch) and are separated by half a diameter (0.44 millimeter or 0.0175 inch) and therefore have a center-to-center spacing CC of 1.5 diameters (1.33 millimeters or 0.052 inch). In this example, the cross-section of the well 31 of FIG. 2 subtends a circular arc A1 in a range of 30°–180° and preferably an approximately 60° arc (30° either side of vertical center axis 45).

Another feature of the invention accomplishes relatively accurate depth sensing and cancels out the effect of varying concentrations of deicer or other impurities in the precipitation.

In FIG. 5 conductances G1 and G2 are measured less preferably over approximately the same distances CC1 and CC2 by two separate pairs of electrodes. FIG. 6 shows that the curves for conductances G1 and G2 are approximately the same shape. Increasing the diameter (breadth) of the exposed portions of electrodes across which conductance G1 is measured merely increases the conductivity as shown by dashed curve 49 without significantly changing the shape of the conductance curve as a function of the depth.

Two conductances G1 and G3 (or G1 and G4 in FIG. 5) are advantageously measured over very different distances by means of two pairs selected from the set of electrodes. In FIG. 7, the electrodes shown are first, second and third electrically conductive pins 51, 53 and 55 embedded in the block 3. In this way the sensor has at least one additional conductor 55 embedded in the block 3 and exposed to the precipitation. The pins have center-to-center spacings CC1 and CC3. The center-to-center spacing CC3 between the second and third pins 53 and 55 is at least ten times the center-to-center spacing CC1 between the first and second pins 51 and 53. The three pins 51, 53 and 55 lie on substantially the same straight line with the second pin 53 between the first and third pins 51 and 55. Two of the conductors or pins 51 and 53 are in a preferred embodiment separated by no more than one millimeter. The particular pair of the conductors or pins 53 and 55 are separated by at least ten millimeters.

FIG. 8 shows that the curve for conductance G3 (or G4) is advantageously very different in shape as a function of depth, when contrasted with the curve for conductance G1. In this way a sensor is provided with at least three electrical conductors terminating substantially flush with the top surface of the block with the conductors having exposed portions that are exposed to the precipitation. A first distance separates the exposed portions of two of the electrical conductors and a second distance separates the exposed portions of a particular pair of the electrical conductors wherein the second distance is at least ten times the first distance. The diameter (breadth) of all of the conductors can be the same in some embodiments, or different in other embodiments.

Circuitry, suitably embedded in the block itself, is connected to the electrical conductors for measuring a first quantity related to electrical conductance between the two electrical conductors that are separated by the first distance and a second quantity related to electrical conductance between the particular pair of conductors that are separated by the second distance which is at least ten times the first distance, and for generating an output signal indicative of precipitation condition as a joint function of the first and second quantities.

One example of a joint function represents precipitation depth as a function of a conductance ratio G3/G1 of the conductance G3 of precipitation over a first distance between pins 53 and 55 to the conductance G1 of precipitation over a second much smaller distance between pins 51 and 53.

FIG. 9 shows that the conductance ratio G3/G1 of FIG. 7 varies over a substantially range 61 of ratio values corresponding to a relatively wide depth sensitive region 63 of different precipitation depths on the top surface 5 of block 3. (Similar advantageous results are obtained by forming the ratio G4/G1 or the ratio G4/G2 in the system of FIG. 5.) This feature is advantageously used in depth measurement by electronically computing a ratio value RV1 at any given time. Then reference to the curve G3/G1 yields a measured depth value DV1. By contrast, a less preferable approach of measuring a conductance ratio G2/G1 in FIG. 5 only provides a slight jog in ratio in FIG. 9 over a narrow range of depths 67. Increasing the diameter of the pair of pins between which one of the conductances is measured in FIG. 5 lowers the overall level of the ratio to a curve 69, but does not significantly widen the narrow region 67. The horizontal areas of ratio curves for G3/G1 and G2/G1 have a relatively high measurement error for depth measurement purposes, and attention is thus focused primarily on the ramping portions of the ratio curves.

In a further improvement shown in FIG. 10, well 31 is provided over two embedded conductors 71 and 73 terminating in well 31 and having a separation S1 for measuring conductance G1. A third conductor 75 is also embedded in block 3 and terminates outside well 31. Conductor 75 is separated from conductor 73 by a distance S2 that is at least ten times greater than separation S1, for conductance measurements between conductor 73 and 75. Providing the top surface 5 of block 3 with well 31 gathers precipitation around the two electrical conductors 71 and 73 and not conductor 75, thereby diminishing the influence of depth of precipitation on the conductance between the conductors 71 and 73 in the well 31. The influence of depth remains substantial, however, on conductance between conductors 73 and 75, as indicated by long gently-curved arrows of current density joining conductors 73 and 75.

Advantageously, the presence of well 31 differentiates the depth dimension into two variables DEPTH1 and DEPTH2. DEPTH1 is the depth of the precipitation measured from the bottom of well 31. DEPTH2 is the depth of the precipitation as measured from the rest of top surface 5 outside of well 31.

In FIG. 11, the relationship of conductance G3 to DEPTH2 is essentially the same as the graph of G3 shown in FIG. 8. Advantageously, however, the graph of conductance G1 is moved leftward in the graph of FIG. 11 compared to the graph of G1 in FIG. 8. When the ratio of conductances G3/G1 is graphed as in FIG. 14, it has an augmented ratio range 81 and a widened depth sensitive region 83 wherein the ratio of conductances varies with depth even at depths near zero. By analogy with FIG. 9 a ratio value RV2 is measured. Then a measured depth DV2 is generated or computed from ratio value RV2 according to the function represented by the curve of FIG. 12. Consequently, the combination of well and electrodes with at least 10:1 distances provides an assembly which is very well suited for depth measurements of relatively thin, as well as moderate, accumulations.

Furthermore, the use of deicers does not appreciably affect the depth measurement process. In FIG. 13, precipitation with deicer 91 covers well 91 and sensor pins 71, 73 and 75. Conductances G1 and G3 are both proportionately increased in FIG. 14, but the shape of the curves for G1 and G3 as a function of depth in FIG. 14 are not significantly different from FIG. 11. Therefore, the ratio G3/G1 shown in FIG. 12 equally represents the ratio computed from the curves of FIG. 14. Consequently, the embodiment of FIG. 10 provides relatively high accuracy of depth measurement over a wide depth sensitive region 83 while affording substantial freedom from effects of impurity concentrations on depth measurement.

Figure 15A:
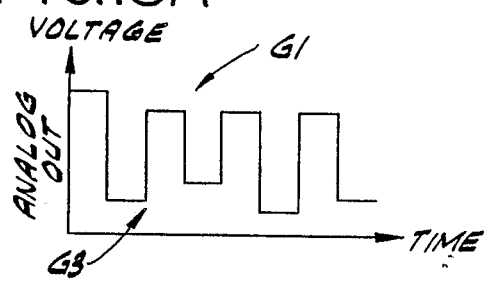
FIG. 15A is a waveform diagram of voltage versus time for an output signal ANALOG OUT in FIG. 15.
Figure 15:
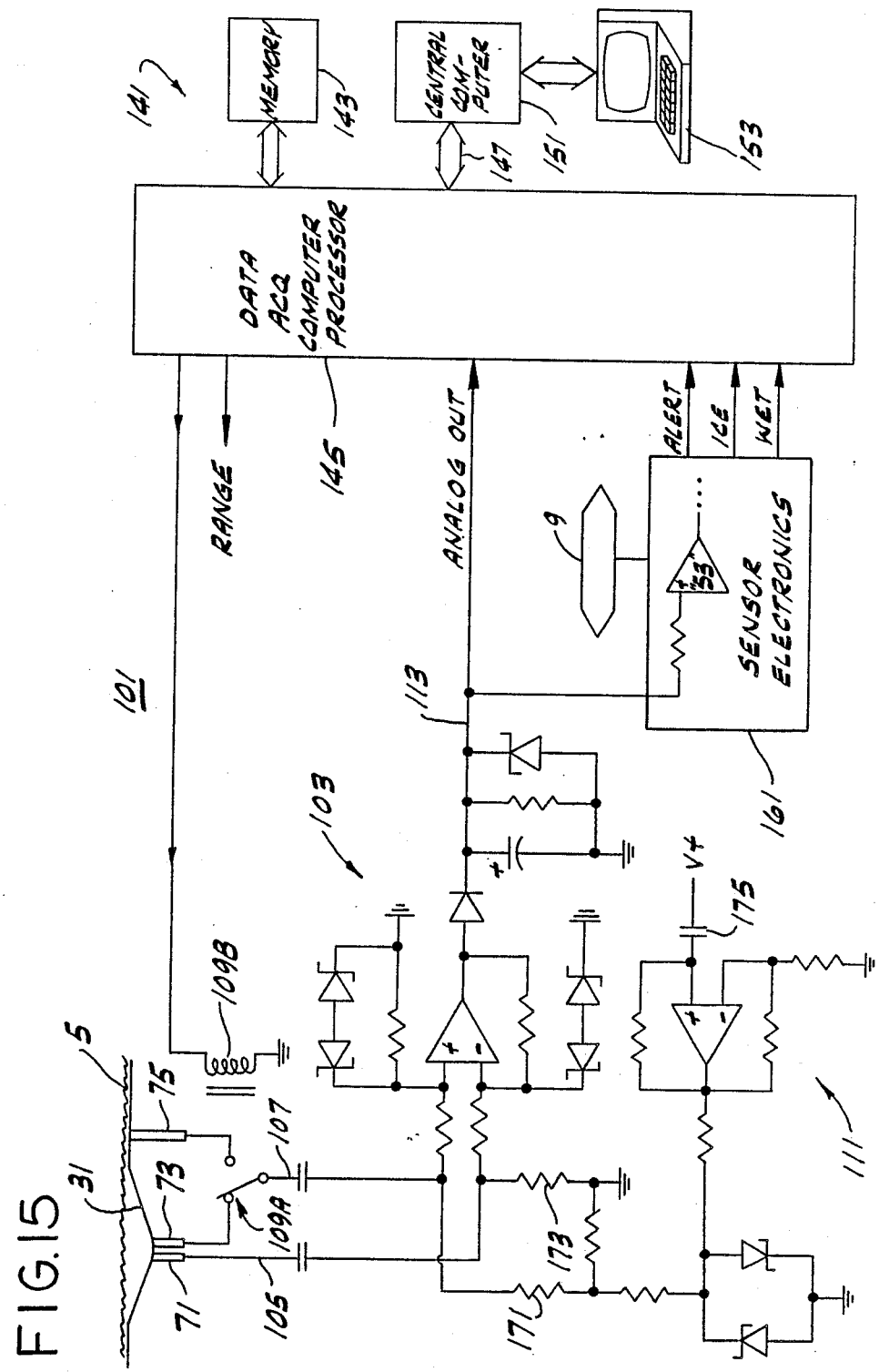
FIG. 15 is a schematic diagram of electronic circuitry connected to the precipitation sensor of FIG. 1, with a block diagram of computers and a display terminal, all according to the invention.

In FIG. 15 electronic circuitry 101 includes a balanced differential amplifier 103 having a pair of inputs 105 and 107 connected across a pair of the electrical conductors 71,73 or 73, 75. An SPDT (single pole double throw) relay has contacts 109A and coil 109B. The SPDT relay acts as an electrical switch for selectively connecting the conductors 73 or 75 to the differential amplifier 103 to measure the conductance of precipitation relative to conductor 71 over different first and second distances S1 and S2 (cf. FIG. 10).

An oscillator 111 suitably has a frequency between 1 kilohertz and 1 megahertz, with 2 kilohertz used in one preferred embodiment. The oscillator 111 supplies a low impedance alternating voltage between conductor 71 and the selected electrical conductor 73 or 75. The balanced differential amplifier 103 produces an analog electrical output ANALOG OUT on a line 113 as a function of conductance of the precipitation across the selected pair of the electrical conductors 71, 73 or 71, 75.

Because of the fixed positions of the conductors 71, 73 and 75 and the fixed dimensions of well 31, the output ANALOG OUT is also representative of the conductivity of the precipitation. In this way circuit 103 measures a physical property of the precipitation itself. Since the conductivity is the reciprocal of resistivity, the output ANALOG OUT is also representative of the resistivity as an inverse function thereof. Put another way, circuit 103 measures a quantity, which is related to the conductance, or is a function of the conductance, between the pair of conductors. The output ANALOG OUT is representative of the quantity sensed.

FIG. 15A graphically shows that the switching by relay contacts 109A effectively causes the output ANALOG OUT to be a multiplexed combination of electrical signals marked on the graph as G1 and G3 representing measurements of conductances G1 and G3 over time. Thus, circuit 103 in FIG. 15 is connected to the conductors 71, 73 and 75 for producing these respective multiplexed electrical signals as a function of the conductances (e.g., G1 and G3) over first and second distances (e.g., S1 and S2).

Further in FIG. 15, a first digital data acquisition computer 141 has a memory 143 for storing preestablished information relating depth to a conductance ratio G3/G1 of conductances of the precipitation over the first and second distances respectively. A processor 145 of computer 141 controls the state of energization of relay coil 109B. Processor 145 is also connected to receive the output ANALOG OUT of electrical circuit 103. Processor 145 develops an electrical signal representing a computed value of the conductance ratio G3/G1 and accesses the memory 143 with the computed value to obtain a measured depth of the precipitation. Then processor 145 outputs a signal on a communications channel 147 representing depth in response to the multiplexed electrical signals. Moreover, processor 145 uses the signal representative of the conductance G1 between the conductors 71 and 73 in well 31 to produce a signal to communications channel 147 indicating an estimated freezing point of the precipitation as a function of the conductance of the precipitation. The estimated freezing point is relatively reliable because the depth amplification and precipitation storage properties of the well 31 reduce the effect of precipitation depth on the measured conductance.

A second computer 151 acts as a central computer to collect the depth and freezing point and other information via channel 147 from data acquisition computer 141 and from any other computers or data sources (not shown) to which computer 151 is suitably connected. In this way computers 141 and 151 individually or together act as an example of a digital computing means for processing the output of the electrical circuit 103 to develop information representing a precipitation condition of the pathway. A display terminal 153 is connected to the central computer 151 and displays the information such as freezing point, depth, and precipitation type representing the precipitation condition of the pathway.

Also in FIG. 15 capacitive sensing plate 9, independently of pins 71, 73 and 75, senses whether atmospheric precipitation of any type is present. Either wet precipitation or dry accumulations of snow or ice can be sensed by plate 9. Sensor electronics 161 is connected to sensing plate 9 to produce a first electrical signal ALERT indicative of presence of precipitation. Sensor electronics 161 also provides an electrical output ICE which indicates an icy surface condition in response to the first electrical signal when the ANALOG OUT electrical signal decreases to and reaches a predetermined ice threshold magnitude. Otherwise, an electrical output WET is produced. The sensor electronics 161 is described in detail in coassigned U.S. Pat. No. 4,281,286 in connection with FIGS. 3A, 3B, 3C and 3D for instance, and said patent is incorporated herein by reference. For the present purposes circuitry 103, 111 of FIG. 15 herein has line ANALOG OUT connected to the noninverting (+) input of op amp "53" in FIG. 3B of said patent in substitution for impurity detector 23 of that FIG. 3B. The incorporation of circuitry from said patent is shown in block form as sensor electronics 161 in FIG. 15 herein. It is to be understood that the functions of sensor electronics 161 can also be performed by computer 141 programmed with appropriate software.

In a further feature, processor 145 takes data from circuit 103 in plural measurement ranges. In such version of apparatus 101, processor 145 has a RANGE output to actuate a relay (not shown). The relay has contacts which simultaneously switch resistors (not shown) in parallel with resistors 171 and 173 and also switch a capacitor (not shown) in parallel with a frequency-setting capacitor 175 of oscillator 111. In this way, accuracy of measurement is enhanced under varying precipitation conditions.

Figure 16:
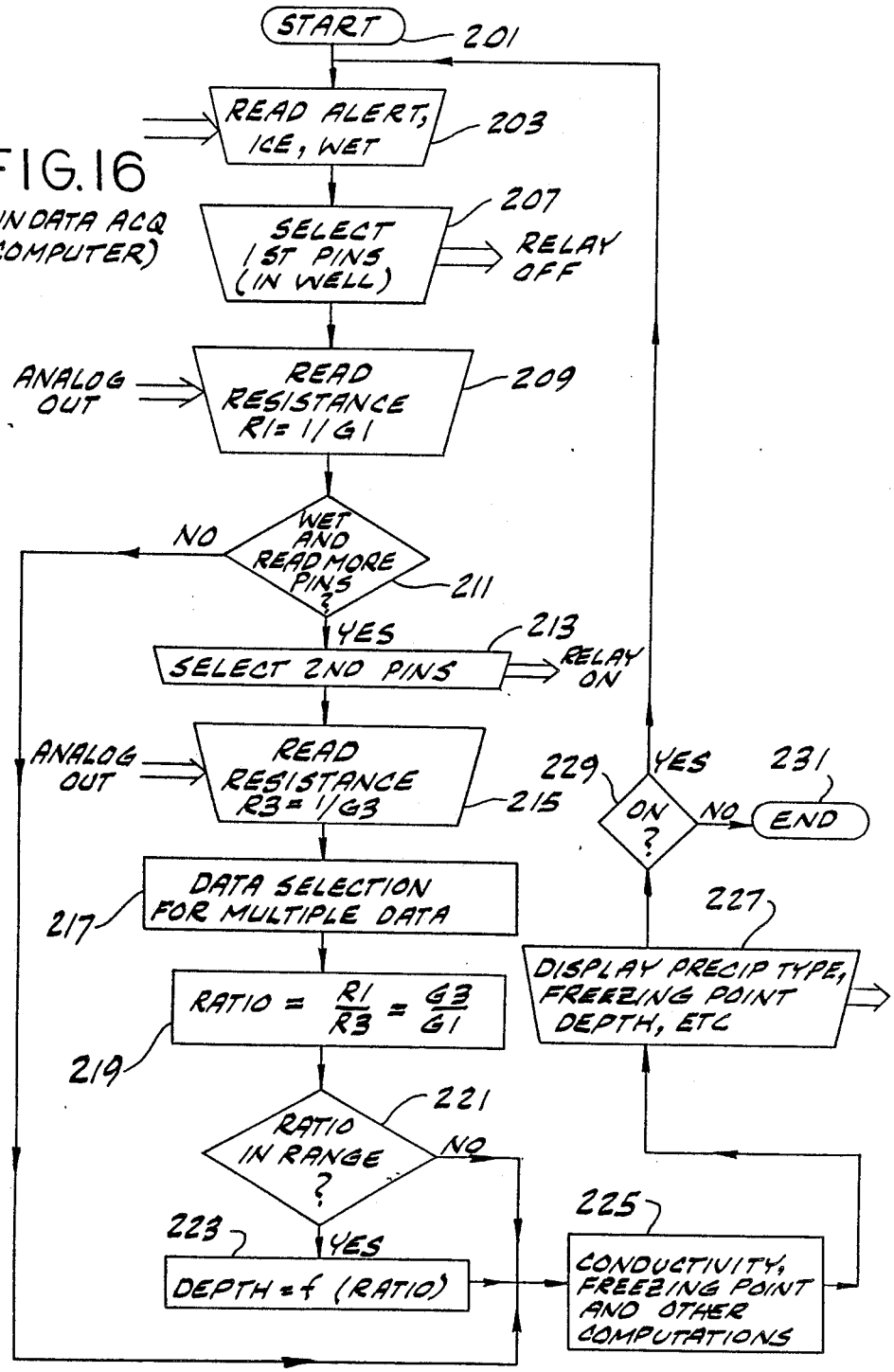
FIG. 16 is a flow diagram of inventive method steps for operating the inventive apparatus of FIGS. 1 and 15.

In FIG. 16 operations commence in computer 141 of FIG. 15 with a START 201 and proceed in a step 203 to read in the inputs ALERT, ICE and WET from sensor electronics 161 of FIG. 15. Operations then proceed to a step 207 to deenergize relay coil 109B (if not already deenergized) so that pins 71 and 73 in well 31 are connected to circuit 103. Next a step 209 reads the level of output ANALOG OUT from circuit 103. A sample-and-hold circuit and analog-to-digital converter (ADC) (not shown) in processor 145 are suitably operated automatically for this purpose. Step 209 also provides a digital representation of a resistance R1 (or its reciprocal, conductance G1).

Next a test step 211 determines whether both of two conditions are present. The first condition is a WET condition from step 203. The second condition is the presence of a flag calling for conductance-based depth measurement from at least one additional conductor pin. The flag is either preestablished in software, established by an electrical jumper, or selected by a user, for example. If both conditions are present in test step 211, operations proceed to a step 213 which energizes relay coil 109B so that pins 75 and 71 are connected to circuit 103 of FIG. 15. Next, a step 215 analogous to step 209 reads the level of output ANALOG OUT and provides a digital representation of a resistance R3 between pins 75 and 71 (or its reciprocal, conductance G3).

An optional further data gathering step 217 selects further pairs of pins (such as those shown in FIGS. 2, 5 and 17-19). Step 217 collects data from the further pins. Step 217 suitably discards and/or averages the data so that the most reliable values are made available for computational purposes.

A succeeding computation step 219 electronically calculates the ratio of resistances R1/R3 or the ratio of conductances G3/G1 or any value which is a suitable function of either of these ratios. A test step 221 then determines whether the ratio value is within the usable range 61 of FIG. 9 or the usable range 81 of FIG. 12. If so, operations proceed to a calculation step 223 that electronically computes precipitation depth by lookup table, polynomial approximation, or any other suitable procedure from the ratio value of step 219. Such calculation in effect utilizes prestored information representing the function of FIG. 9 or FIG. 12, for example. A calculated ratio value RV1 in FIG. 9 is thus used to obtain a calculated depth value DV1 from the function of FIG. 9. If FIG. 12 is applicable, a calculated ratio value RV2 is used to obtain a calculated depth value DV2.

The computer 141 in step 225 of FIG. 16 is programmed by the skilled worker to look up or otherwise compute the conductivity, deicer concentration, and estimated freezing point from the measured conductance G1 or resistance R1 obtained from output ANALOG OUT from circuit 103. The freezing point of wet precipitation is depressed by an amount depending on the concentration and type of deicer in the precipitation. Some typical deicers are sodium chloride (NaCl), calcium chloride ($CaCl_2$), calcium and magnesium acetates, and deicers including mixtures of ethylene glycol and/or diethylene glycol with corrosion inhibitors. A designation of the particular deicer is prestored in memory 141 for a given user, or entered by the user directly. The sensor is calibrated with known solutions in well 31 and by entering appropriate calibration constants or data in memory 141 so that the conductivity (or specific conductance in mhos per centimeter) corresponding to the resistance R1 or the conductance G1 is correctly determined by computer 141 in in step 225. The concentration of deicer is computed as a function of the computed conductivity. The functional relationships of concentration-versus-conductivity and of freezing-point-versus-concentration are tabulated in readily available chemical reference works. The freezing point is computed from the deicer concentration, or directly from the conductivity using these known relationships.

When the ratio value is out of range 61 (or 81) in step 221, operations branch directly to step 225 and bypass the depth calculation of step 223. Also, if in step 211 the precipitation is not WET, operations branch directly to step 225 and bypass the depth calculation. Similarly, in step 211 the branch occurs to step 225 if no pins outside of the well 31 are to be selected for conductance measurement.

After step 225, a step 227 sends the information developed about precipitation type, freezing point, precipitation depth, deicer concentration and so on, to central computer 151 for eventual display on terminal 153. Operations FIG. 16 loop back from step 227 through an ON-test step 229 to step 203 unless processor 145 is turned off, whence operations branch from step 229 to an END 231.

Figure 17:
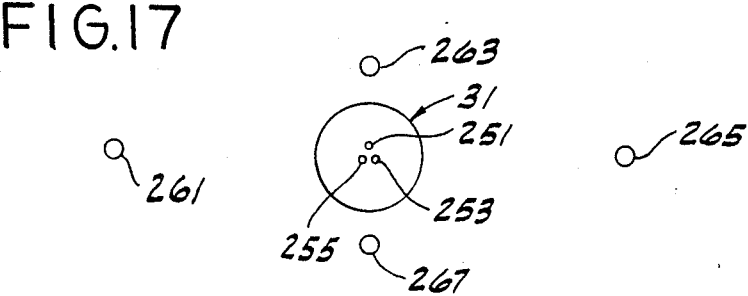
FIG. 17 is a plan view of an alternative arrangement of sensor conductors and a well in the top surface of a block of inventive apparatus.

In FIG. 17, an alternative embodiment, analogous to the block of FIG. 2, has well 31 provided with a triad of pins 251, 253 and 255 at vertices of an equilateral triangle centered in the well 31. Outside the well 31 are four pins 261, 263, 265 and 267 having their centers at vertices of a rhombus centered with respect to the well 31. Numerous combinations of the pins 251, 253, 255, 261, 263, 265 and 267 are electronically selected for measurement of conductances over various distances. The measurements are then processed by an averaging or other suitable algorithm for substantial reliability. The accuracy of depth measurements is also suitably enhanced by using prestored tables of plural conductivity ratios developed from measurements over the various distances and applying a statistical analysis in step 225 of FIG. 16.

Figure 18:
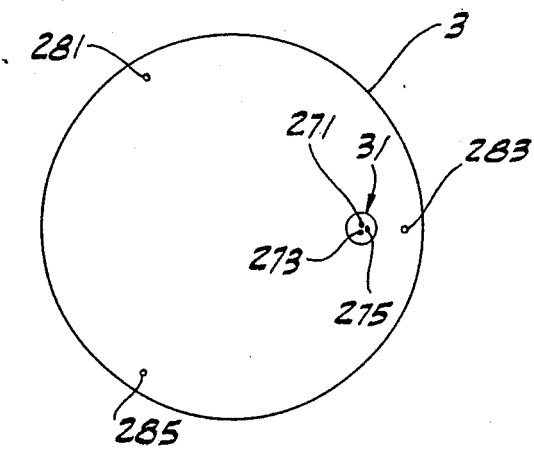
FIG. 18 is a plan view of an additional alternative arrangement of sensor conductors and a well in the top surface of a block of inventive apparatus.

FIG. 18 shows a further alternative pin geometry using the entire surface of block 3. Well 31 gathers precipitation for a closely spaced triad of pins 271, 273 and 275 centered therein. A larger triad of pins 281, 283 and 285 have their centers at the vertices of an equilateral triangle nearly spanning the entire block 11. One of the pins 283 is located near well 31. This geometry permits conductivity measurements within the triad in the well over a first, relatively minute, distance. Another measurement between pin 275 and pin 283 provides conductance over a second distance about ten times the first distance. Further measurements in the larger triad of pins 281, 283, 285 provide conductance over a third distance about ten times the second distance.

In another embodiment two pairs of pins as in FIG. 5 are located at a distance apart which is at least ten times the pin spacing in either pair. Conductance measurements are made within pairs and between pairs. A ratio of between-pair conductivity to within-pair conductivity is also derived.

In still other embodiments, not shown, some or all of the pins are replaced with other electrical conductors having exposed bars, regular polygons, concentric circles, displaced rings, or other geometries and combinations thereof as the skilled worker elects in the practice of the present invention.

Figure 19:
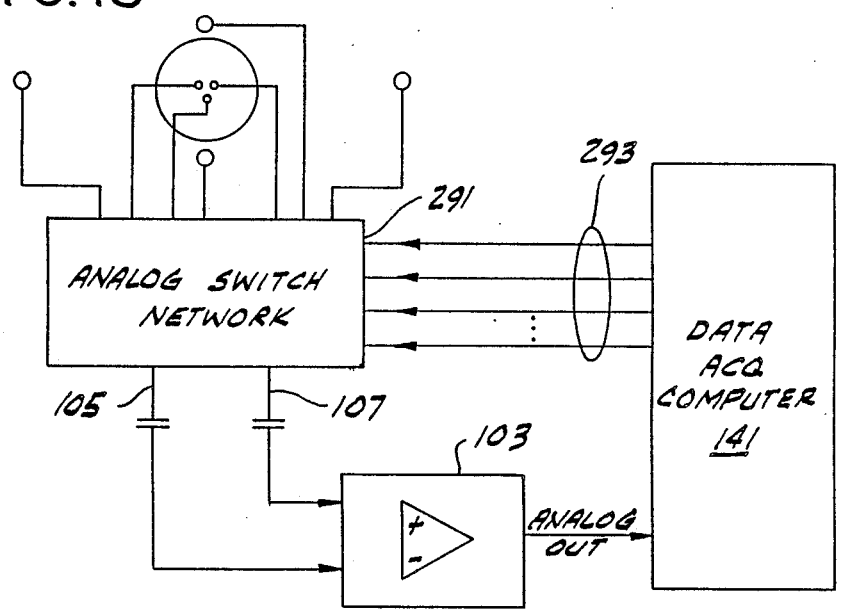
FIG. 19 is a block diagram of inventive apparatus for operating the sensor of FIG. 17.

In FIG. 19, the relay contacts 109A and relay coil 109B of FIG. 15 are replaced with an analog switch network 291 using commercially available integrated circuit technology. The pin configuration of FIG. 17 (or FIG. 18 or otherwise) is connected to the analog switch network 291. Network 291, under control of computer 141 via a bus 293, connects one or more selected pins to inputs 105 and 107 of balanced differential amplifier 103. The number N of lines in bus 293 can carry a parallel digital signal representing any of $2^N$ states for controlling network 291. Computer 141 sequentially sends different bytes to network 291 to select different sets of two or more pins at a time for conductance measurements. In this way, numerous measurements are multiplexed to form output ANALOG OUT of circuit 103.

Figure 20:
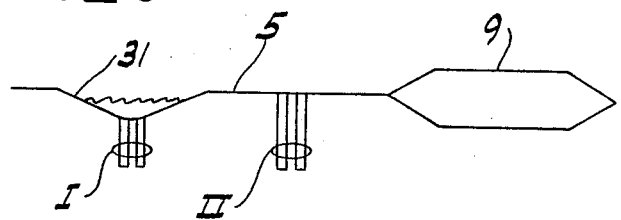
FIG. 20 is a sketch of a multiple-pin conductance sensor and a capacitance sensor for characterizing precipitation.
Figure 21:
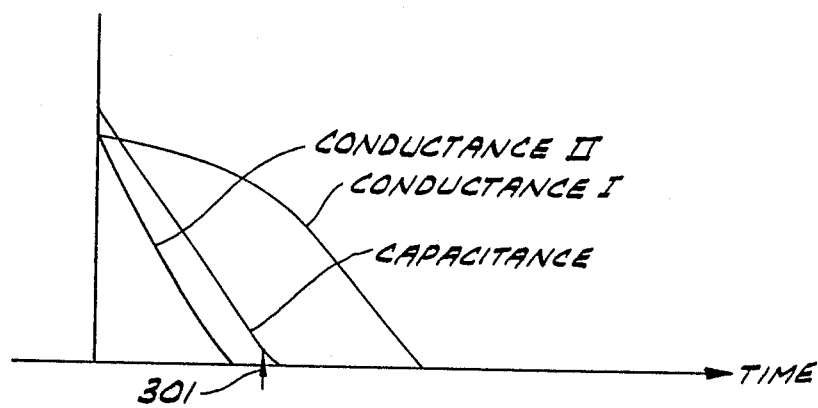
FIG. 21 is a graph of capacitance and conductance versus time as a layer of precipitation dries on the surface of a block improved with a well according to the invention of FIG. 20.

FIGS. 20 and 21 illustrate further advantageous features of those embodiments using conductance-measuring circuitry with a precipitation-gathering well 31 and a capacitance sensor 9. In FIG. 20, a pair of sensing pins I are beneath the well 31. Another pair II of the sensing pins terminate on a flat portion of surface 5. Advantageously, in FIG. 20, well 31 temporarily stores the precipitation therein.

In a scenario of drying in FIG. 21, this storage function of well 31 extends the presence of high conductance (see Conductance I) between pair of pins I past a time 301 when a remnant of precipitation is still sensed by capacitance sensor 9 on the rest of the surface 5. When capacitance sensor 9 senses that the top surface of the block is dry, there is no ambiguity of interpretation (as DRY) even though the contents of well 31 are wet (conductive). Moreover, this approach is useful with or without a temperature sensor in situations near freezing. Also, the approach is useful in situations in which the freezing point of liquid on surface 5 may be unknown because the liquid is very thin and has a steadily increasing deicer concentration increasing up to saturation as drying proceeds.

In exacting applications, further considerations should also be noted. If the well is full of liquid water and the surface above capacitance sensor 9 has a thin layer of wet precipitation on it, then the thin wet layer could freeze before the contents of the well. The well contents would be conductive and the sensor would sense the presence of precipitation, thus potentially leading to an interpretation that no freezing had occurred. Advantageously, one or more additional pins such as pair II outside the well provide further conductance information conductance II.

The data for characterizing surface condition is thus suitably interpreted by hardware logic appropriately implemented in substitution for sensor circuit 161 or by software logic in step 225 of FIG. 16 according to the following Precipitation Table:

| PRECIPITATION TABLE | | | |
|---|---|---|---|
| G: PINS IN WELL | G: PINS ON TOP SFC. | C: CAP SENSOR | Top Surface Precip. Condition |
| low | low | low | Dry |
| low | low | high | Ice |
| low | high | low | Abnormal |
| low | high | high | Wet |
| high | low | low | Dry |
| high | low | high | Ice |
| high | high | low | Abnormal |
| high | high | high | Wet |

The above table is also complemented with temperature data in further embodiments.

Figure 22:
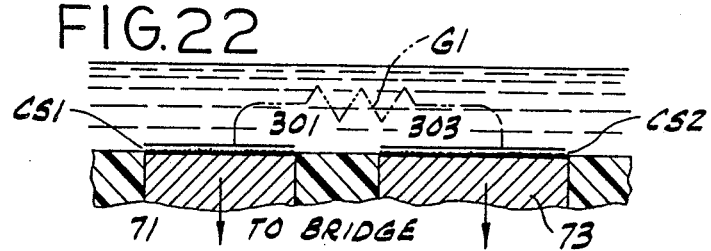
FIG. 22 is a greatly magnified cross-section of sensor conductors in the well, with electrical symbols and indicating a dielectric buildup due to corrosion which produces a series capacitance in the presence of precipitation.

FIG. 22 shows a possible complication in characterizing precipitation. Corrosion films 301 and 303 of irregular and indefinite thickness on the order of micrometers ($10^{-6}$ meter) form on the exposed portions of the conductors 71 and 73 and endow them with a series capacitance Cs1 on conductor 71 and a series capacitance Cs2 on conductor 73 in the presence of precipitation. If the corrosion accumulates excessively, conductance measurements in FIG. 15 are reduced in accuracy. The corrosion forms an invisible dielectric film or barrier with a dielectric constant on the order of 5 to 10 times that of free space. The film may be pierced irregularly by tiny channels of conductivity, further complicating the analysis process.

The precipitation itself has a conductance G1 and provides the conductive equivalent of a virtual capacitor plate indefinite in thickness adjacent to corrosion films 301 and 303. In the absence of precipitation, a relatively minuscule capacitance exists between conductors 71 and 73, not to be confused with the larger series capacitance $Cs = 1/((1/Cs1) + (1/Cs2))$.

Figure 23:
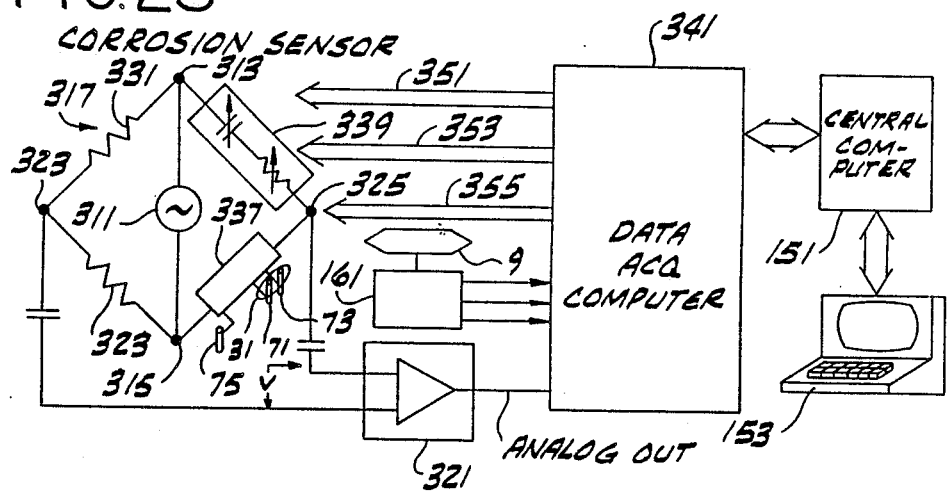
FIG. 23 is a schematic diagram of an alternative electrical circuit of the invention for making measurements of conductance and series capacitance by an electrical bridge network under control of a computer operating by a method of the invention.

In FIG. 23, a preferred embodiment not only measures the conductance (or resistance) of the precipitation when present, but also measures the series capacitance Cs and produces a warning when the series capacitance in the presence of precipitation is less than a predetermined capacitance indicative of excessive corrosion.

An oscillator 311 is connected at points 313 and 315 to an electrical bridge 317 energized from the oscillator 311. A detecting circuit 321, such as a balanced differential amplifier like circuit 103 of FIG. 15, is connected to the bridge 317 at two other points 323 and 325 to detect or sense whether the bridge 317 is balanced, or nulled. A voltage V between points 323 and 325 represents the depth of null of the bridge 317. Analog level ANALOG OUT at the output of detecting circuit 321 depends on the depth of null (represented by voltage V) of the bridge 317.

In bridge 317 two resistors 331 and 333 are connected from point 323 to points 313 and 315 respectively. A set of conductors including conductors 71 and 73 in well 31 are connected to an analog switch circuit 337 which has inputs connected to points 315 and 325 of bridge 317. The impedance across conductors 71 and 73 in well 31, for example, has a capacitance value and a resistance value (as in FIG. 22) due to the series capacitance Cs and the resistance (or conductance G1) of any precipitation.

For balancing the bridge 317, an adjustable impedance circuit 339 has a variable or adjustable capacitance section and a variable or adjustable resistance section. A bank of resistors which are connected in parallel by analog switches (not shown) form the variable resistance section. A bank of capacitors which are connected in parallel by further analog switches (not shown) form the variable capacitance section. Circuit 339 is connected between points 313 and 325 of bridge 317. A data acquisition digital computer 341 is connected to the output of detecting circuit 321, and supplies control signals to analog switch circuit 337 to select sensor conductors, e.g., pair 71, 73 or pair 73, 75. The depth of null represented by voltage V depends on the adjustable value of resistance and capacitance in circuit 339. Computer 341 acts as an electronic control and sends control signals on buses 351 and 353 to the analog switches in circuit 339 to vary the impedance of the circuit 339 part of bridge 317 until the detecting circuit 321 detects that the bridge is substantially balanced.

In this way the computer 341 determines binary values of control signals on buses 351 and 353 that respectively establish the particular capacitance value and particular resistance value of the circuit 339 that most deeply null the bridge 317. The capacitance and resistance of the circuit 339 thus determined are respectively proportional to the series capacitance Cs and resistance of the precipitation across the conductors, e.g., 71 and 73 selected by circuit 337. In this way, computer 341 determines the particular capacitance value and the particular resistance value at which the bridge is most deeply nulled. Given the particular capacitance value, the computer 341 supplies a signal indicating whether or not the series capacitance is less than a predetermined value indicative of abnormal conditions such as excessive corrosion, or fouling of the sensor or malfunction. Computer 341 also computes and produces a further electrical output representative of freezing point of the precipitation as a function of the particular resistance value determined, as described in connection with step 225 of FIG. 16. Capacitive sensor 9 and sensor electronics 161 provide ALERT, ICE and WET signals to computer 341 in the manner already described in FIGS. 15 and 16. Computer 341 supplies its output to central computer 151 which in turn displays data on video terminal 153.

Figure 24:
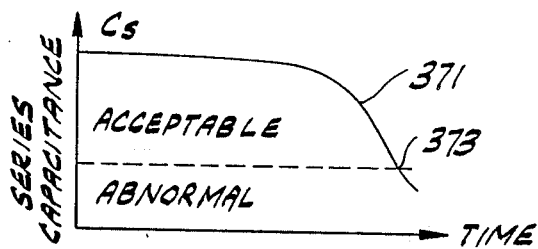
FIG. 24 is a graph of series capacitance of FIG. 22 versus time.

FIG. 24 illustrates that the series capacitance Cs is normally high in a region marked Acceptable. If excessive corrosion occurs over time, then the series capacitance falls in a curve portion 371 and reaches a point 373 where it enters a region marked Abnormal. Computer 341 provides a warning when the series capacitance enters the abnormally low region.

Figure 25:
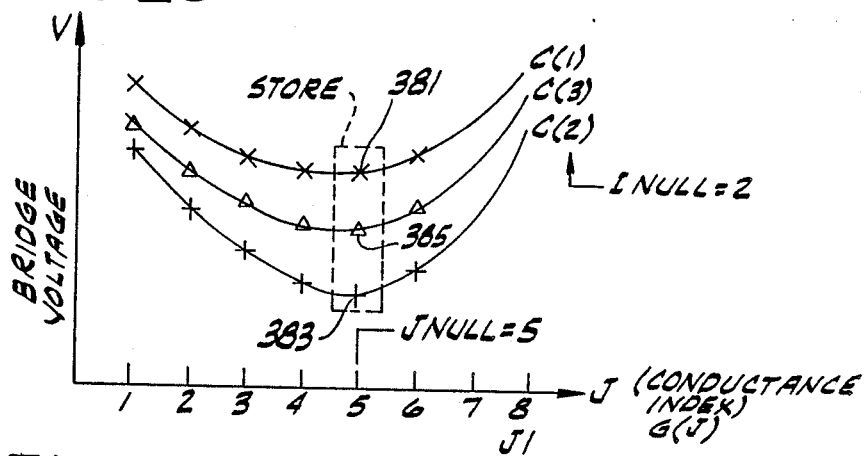
FIG. 25 is a graph of a bridge voltage versus a conductance index J showing a family of curves for different bridge capacitances and illustrating a method of operation of the computer of FIG. 23.

FIG. 25 graphically illustrates the operations of computer 341 when the series capacitance Cs is in the acceptable range. Computer 341 starts with a lowest value of capacitance C(1) in the capacitance section of circuit 339 of FIG. 23 by sending a parallel digital signal thereto on bus 351 of FIG. 23. Without changing capacitance C(1), computer 341 sends a series of control signals on bus 353 to vary the conductance G(J) of the resistance section of circuit 339. The control signals on bus 353 correspond to a series of index values J in FIG. 25. The voltage V from bridge 317 decreases to a null and then begins to rise, for example at J=6 in FIG. 25. This means that the null is found at J=5.

Next, computer 341 increments the capacitance section of circuit 339 to a value C(2) and finds a deeper null 383 by again varying the conductance through index values J, starting with index J=1. Then computer 341 increments the capacitance section to a value C(3) and illustratively finds a shallower null 385. This means that the deepest null was null 383. Consequently, the capacitance value C(2) is the best estimate of the series capacitance of selected conductors, such as 71 and 73. The null 383 occurs at an index J value of 5, indicating that conductance value G(5) is the best estimate of the conductance of the precipitation between the selected conductors 71 and 73.

Figure 26:
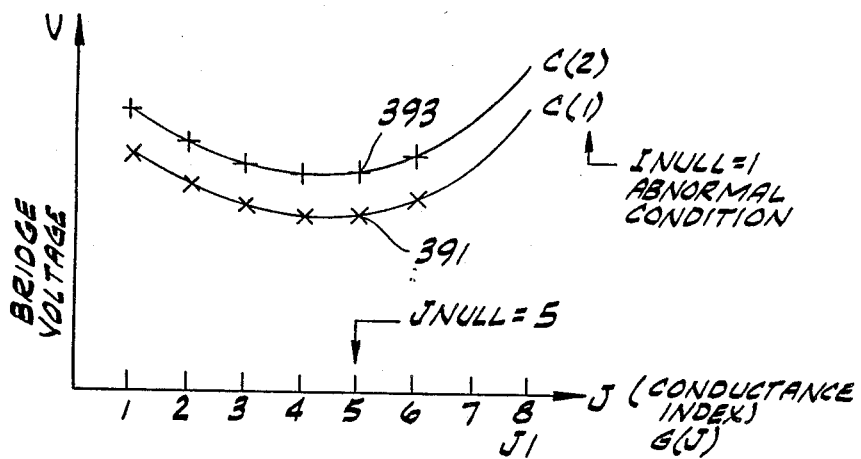
FIG. 26 is a graph of bridge voltage versus conductance index J showing a family of curves for different capacitances and illustrating a method of operation of the computer of FIG. 23 under an abnormal condition of low series capacitance of the conductors exposed to the precipitation.

FIG. 26 illustrates measurements that occur when the series capacitance falls into the abnormal region of FIG. 24. The deepest bridge null 391 occurs at the least value of capacitance C(1). With capacitance C(2), a higher, shallower null 393 is detected. As soon as the null 393 at capacitance C(2) is detected and found to be higher than null 391, operations conclude that the series capacitance Cs is abnormally low.

Figure 27:
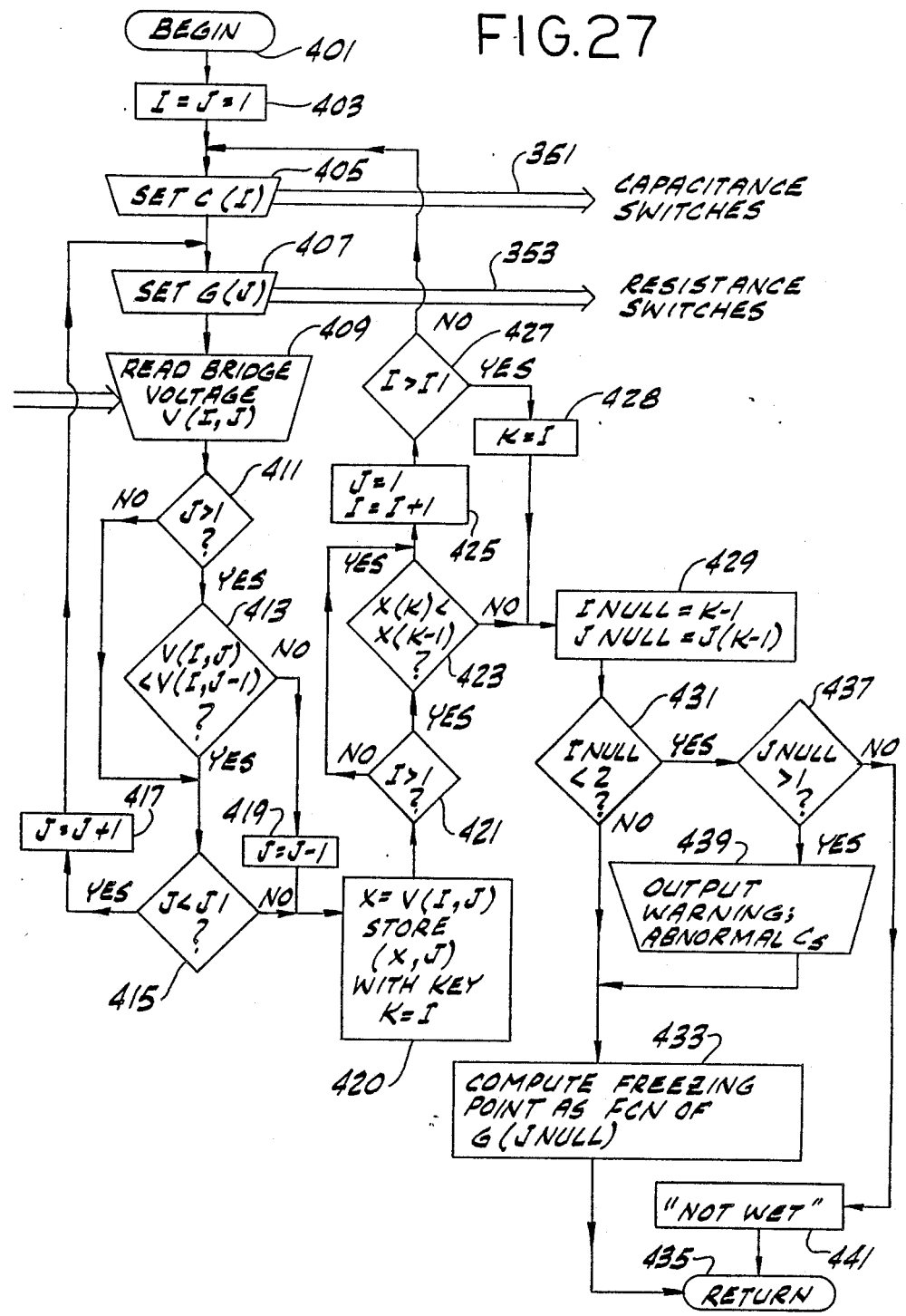
FIG. 27 is a flow diagram of inventive method steps for operating the inventive apparatus of FIGS. 1 and 23.

FIG. 27 shows a flowchart of the operations of computer 341 in a subroutine suitably added to software for computer 341 and called in steps 209 and 215 of FIG. 16. (FIG. 16 is applicable to computer 341 of FIG. 23 as well as computer 141 of FIG. 15.) Operations in FIG. 27 commence with a BEGIN 401 and proceed to an initialization step 403 to set a capacitance index I and a conductance index J both to unity (1). Then a step 405 sends a parallel digital signal representing index I on bus 351 to the analog switches for setting the capacitance section to a capacitance value C(I) in circuit 339 of FIG. 23. A succeeding step 407 sends a parallel digital signal representing conductance index J on bus 353 to analog switches for paralleling resistors in the resistor bank section to obtain a conductance G(J) in circuit 339.

Operations proceed to an input step 409 to read in the bridge voltage V from detecting circuit 321 by analog-to-digital conversion of ANALOG OUT from circuit 321. Then a test step 411 determines whether index J exceeds its initial value, one. If not, operations bypass a comparing step 413 and go directly to a step 415, since there is no previous measurement to compare. Otherwise, when index J exceeds one, operations go from step 411 to step 413 to determine whether the latest bridge voltage V(I,J) is less than the bridge voltage V(I,J−1) wherein circuit 339 had the next previous conductance G(J−1). If less in step 413 (YES), no null is yet determined and operations proceed to step 415 to determine whether index J is less than a prestored number J1. The number J1 is the number of values of conductance index J that can be sent to bridge 317. If index J is less than J1, then a step 417 increments the index J and operations loop back to step 407 in an operational inner loop.

If a null be found in step 413 because the bridge voltage V has begun to rise above the previous voltage V(I,J−1), then operations branch from step 413 to a step 419 to decrement the index J because the null occurred at the next previous value of index J. Operations then proceed to a step 420 to store the value of bridge voltage and index J in a file accessible by the currently existing capacitance index I as a key K. In the absence of a null, all of the index values J are exhausted, without exercising the NO branch from test step 413. Instead, when index J reaches J1, test step 415 causes a branch directly to step 420 to store the last bridge voltage V(I,J1) and greatest index value J=J1, with index I as key K.

Operations go from step 420 to a step 421 to test the capacitance index I. If capacitance index I is its initial value of one, operations bypass a step 423 and go directly to a step 425 to reset conductance index J to one and to increment the capacitance index I to start taking data on a new curve in FIG. 25 or 26. If capacitance index I is greater than one in step 421, operations go to step 423 to determine whether the latest null X(K) is less than the next previous null X(K−1). If so, the deepest null is as yet undetermined, and operations proceed from step 423 to step 425. After step 425 is performed, a test step 427 determines whether all capacitance index I values have been exhausted, by testing whether index I exceeds a maximum prestored number I1. If not, operations loop back to step 405 in an operational outer loop.

If all of the index I values are exhausted, then index I exceeds I1 and operations branch from step 427 to a step 428 to set key value K to the current value (I1+1) of index I whence a step 429 is reached. Also, in step 423, if the null X(K) has begun to rise as a function of capacitance C(I) so that X(K) is not less than X(K−1), then the deepest null is found, and operations branch from step 423 directly to step 429. In step 429 two index values INULL and JNULL are established to identify the deepest null. Index value INULL is a capacitance index that is set equal to one less than the latest key value K because the deepest null is the null previous to any rise in null value detected by step 423. The index value JNULL is a conductance index that is set equal to a stored value of index J in the file of step 420 that has a key value which is one less than the latest key value of key K.

Then a step 431 determines whether the capacitance index INULL is less than 2, indicative of an abnormal condition (cf. FIG. 24). If not, operations proceed to a step 433 to compute the freezing point as a function of the precipitation conductance G corresponding to the index JNULL, whence a RETURN 435 is reached.

If in step 431, the capacitance index INULL is indeed less than 2, operations branch to a step 437 to determine whether the conductance index JNULL exceeds one. If so, conductive precipitation is determined to be present so that the series capacitance Cs is measurable. (If there were no precipitation, the capacitance between dry electrodes would be very low and no conclusion about the series capacitance could be drawn.) With JNULL exceeding unity, operations proceed from step 437 to an output step 439 to output a warning of the abnormal condition, and then go to step 433 to compute a freezing point, if possible. If conductance index JNULL is not greater than one in step 437, operations branch to a step 441 to enter a conclusion "NOT WET" and set a flag for use as a further datum in determining the type of precipitation in steps 225 and 227 of FIG. 16. After step 441, RETURN 435 is reached.

It should be noted that the comparing step 413 is involved in the determination of each point of null 381, 383, 385, 391 and 393 of FIGS. 25 and 26. If noise is substantial, the "less than" comparison of step 413 can be refined by requiring that the test be "less than by at least a preset amount." Even further sophistication can alternatively be provided by taking data over all the curves in FIG. 25, for example, and then estimating the nulls by statistical techniques.

Figure 28:
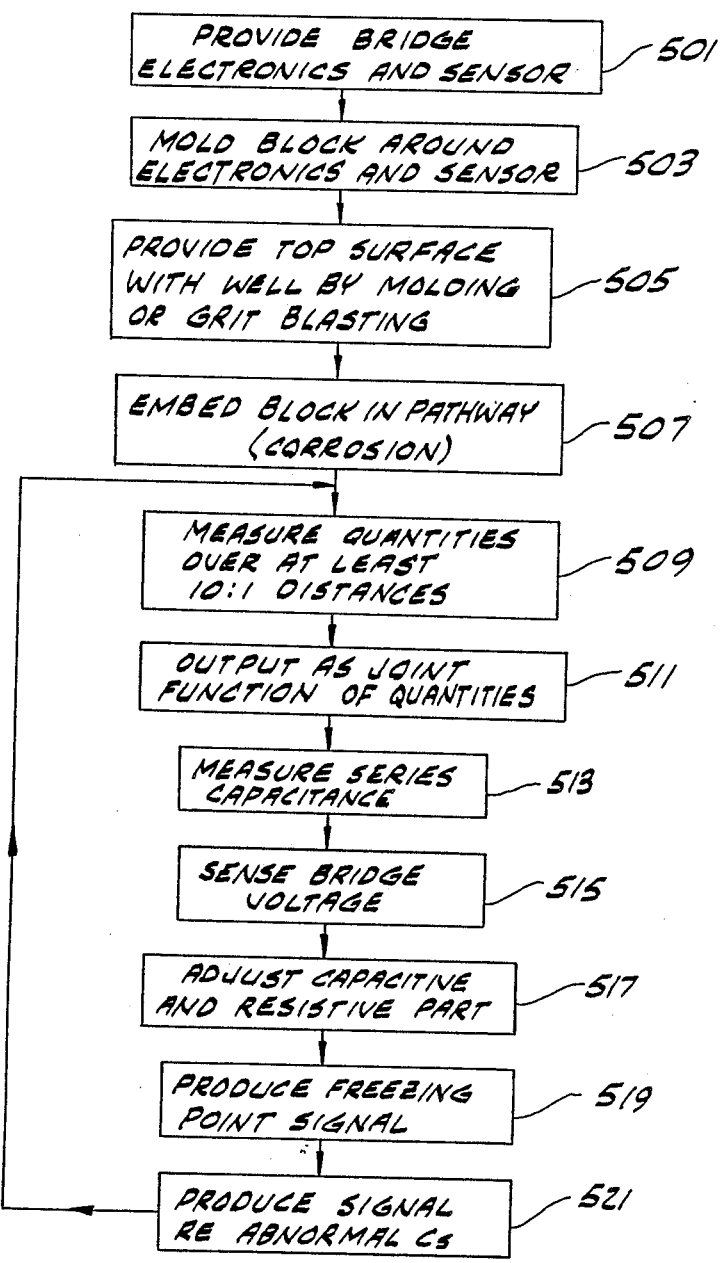
FIG. 28 is a flow diagram of inventive method steps of constructing and operating the inventive apparatus of FIGS. 1 and 23.

FIG. 28 shows a flow diagram further describing and summarizing various aspects of an inventive method of making apparatus and operating it to detect the presence and condition of precipitation on the surface of a pathway.

An initial step 501 provides an adjustable electrical bridge 317 with electrical conductors (e.g., 71, 73, etc.) to sense the precipitation. The precipitation has a freezing point which is a function of an electrical conductance of the precipitation when the precipitation is wet and the electrical conductors have a series capacitance in series with the electrical conductance of the precipitation. The bridge includes an adjustable impedance having an adjustable capacitive section and an adjustable resistive section.

Next in a step 503, a block of electrically insulative material is molded around a sensor embedded therein for sensing a physical property of the precipitation which property is also influenced by the depth of the precipitation. For example, a mold is filled with a curable material around a pair of electrically conductive pins 71 and 73, and the material is cured to produce a block of electrically insulative material having a top surface and adapted to be embedded in a pathway and exposed to precipitation.

The method proceeds to a step 505 of forming a well 31 for gathering precipitation entering the well. The electrically conductive pins 71 and 73 thereby have portions thereof exposed to precipitation gathered in the well. The well 31 in some embodiments is advantageously formed integral with the top surface of the block by including the well shape in the mold and curing the block so that the well is formed by molding. In other embodiments, the well is formed by grit-blasting the pins and their surrounding part of the top surface 5 of the block to form the well. The top surface of the block is thus provided with a well that is generally curved in outline above the sensor for gathering precipitation around the sensor thereby diminishing the influence of precipitation depth on the sensor.

Next, in a step 507 the block of electrically insulative material is embedded in the pathway with the top surface 5 of the block exposed to precipitation. In those embodiments with electrical conductors exposed to precipitation, corrosion forms on the conductors and endows them with a series capacitance in the presence of precipitation. In one preferred embodiment, a block of electrically insulative material is molded around at least three electrical conductors terminating substantially flush with a top surface of the block with the conductors having exposed portions that are exposed to precipitation. A first distance separates the exposed portions of two of the electrical conductors and a second distance separates the exposed portions of a particular pair of the electrical conductors wherein the second distance is at least ten times the first distance.

In the embodiments that have conductors separated by different distances, the method in a step 509 proceeds by measuring a first electrical quantity related to electrical conductance between the two electrical conductors that are separated by the first distance and measuring a second quantity related to electrical conductance between the particular pair of conductors that are separated by the second distance which is at least ten times the first distance.

A step 511 is performed to generate an electrical output signal indicative of a condition of the precipitation as a joint function (such as the ratio, for example), of the first and second quantities. Next in a step 513, the series capacitance in the presence of precipitation is electronically measured by operating bridge 317 as described hereinabove. For measurement purposes, a step 515 senses an electrical voltage V from the bridge 317 indicative of a depth of null of the bridge. Operations proceed in a step 517 by adjusting the capacitance value and the resistance value of the adjustable impedance circuit 339 in the bridge to determine the particular capacitance value and the particular resistance value at which the null is deepest. The particular capacitance value thus determined is related to the series capacitance and the particular resistance value thus determined is related to the conductance of the precipitation.

Following the adjustment of the bridge to find the deepest null, a step 519 produces an electrical output representative of a freezing point of the precipitation as a function of the particular resistance value at which the null is deepest provided the particular resistance value is less than or equal to a first predetermined amount indicative of wet precipitation.

A further step 521 produces an electrical signal indicating whether or not the series capacitance in presence of precipitation is less than a predetermined capacitance value. For example, the signal represents whether or not the particular capacitance value is abnormally low in value, provided the particular resistance value is less than or equal to the first predetermined amount of resistance indicative of wet precipitation. Production of the signal indicates a likelihood of excessive corrosion. Operations then loop back to step 509 to repeatedly derive data from the apparatus.

It is emphasized that the methods of circuit operation shown as flowcharts of computer operations herein are equally applicable in apparatus of the invention implemented entirely in hardware, or in a microprocessor based control programmed with software, or in firmware implementations.

The invention comprehends numerous embodiments which are providable for applications arising now and in the future, so that the utility of the invention can be fully realized.

In view of the above, it will be seen that the several objects of the invention are achieved and other advantageous results attained.

As various changes could be made in the above constructions without departing form the scope of the invention, it is intended that all matter contained in the above description or shown in the accompanying drawings shall be interpreted as illustrative and not in a limiting sense.

What is claimed is:

1. Apparatus for detecting the presence and condition of precipitation on the surface of a pathway, comprising:

a block of electrically insulative material adapted to be embedded in the pathway and having a top surface exposed to precipitation; and sensor means embedded in said block for sensing a physical property of the precipitation to produce a sensor output which is also influenced by a depth of the precipitation, wherein part of the top surface of the block has a well that is generally curved in outline above said sensor means for gathering precipitation for said sensor means, thereby diminishing the influence of precipitation depth on said sensor means.

2. Apparatus as set forth in claim 1 wherein the well is smoothly curved in cross-section with a depth amplification factor exceeding 1.5.

3. Apparatus as set forth in claim 1 wherein said sensor means is embedded in said block substantially flush with a surface of the well.

4. Apparatus as set forth in claim 1 further comprising electrical circuit means connected to said sensor means for producing an output representative of the physical property of the precipitation, digital computing means for processing the output of said electric circuit means to develop information representing a precipitation condition of the pathway, and display means connected to said digital computing means for displaying the information representing the precipitation condition of the pathway.

5. Apparatus as set forth in claim 1 wherein said well has a width that is between 3 and 12 times the well depth.

6. Apparatus as set forth in claim 1 wherein the well has a width that is between 3 and 5 times the well depth.

7. Apparatus as set forth in claim 1 wherein said sensor means includes a pair of conductors having portions thereof exposed to precipitation gathered by the well when precipitation occurs, the exposed portions having a center-to-center spacing and the well having a depth that is at least twice said spacing.

8. Apparatus as set forth in claim 7 wherein the well has a width that is between 3 and 5 times the well depth.

9. Apparatus as set forth in claim 8 wherein the exposed portions have respective centers and a breadth along a line between the centers that is less than the center-to-center spacing.

10. Apparatus as set forth in claim 7 wherein the electrically insulative material comprises a thermosetting synthetic resin material having the well formed as a radially symmetric depression in the synthetic resin material.

11. Apparatus as set forth in claim 1 wherein the well has a well depth and said sensor means includes a pair of conductors having exposed portions thereof exposed to precipitation gathered by the well when precipitation occurs, and the exponductors having exposed portions thereof exposed to precipitation gathered by the well when precipitation occurs, and the exposed portions are separated by a distance which is less than one-half the well depth.

12. Apparatus as set forth in claim 1 wherein the well is smooth and curved, thereby substantially inhibiting deterioration of the well when water therein freezes to ice.

13. Apparatus as set forth in claim 1 wherein the well has a cross-section that has a maximum slope which is between 0.5 and 2.0 in magnitude.

14. Apparatus for detecting the presence and condition of precipitation on the surface of a pathway, comprising:
a block of electrically insulative material having a top surface and adapted to be embedded in the pathway with the top surface of the block exposed to precipitation; and
sensor means for sensing a quantity related to electrical conductivity of the precipitation to produce a sensor output which is also influenced by the depth of the precipitation, wherein part of the top surface of the block is provided with a well for gathering precipitation around said sensor means, thereby diminishing the influence of depth of precipitation on said sensor means, said sensor means including a pair of conductors having portions thereof exposed to precipitation gathered by said well when precipitation occurs.

15. Apparatus as set forth in claim 14 further comprising electronic means for measuring a quantity which is a function of the conductance between the pair of conductors.

16. Apparatus as set forth in claim 15 further comprising means connected to said electronic means for producing a signal indicating an estimated freezing point of the precipitation as a function of the conductance of the precipitation.

17. Apparatus as set forth in claim 14 further comprising electrical circuit means connected to said conductors for producing an output representative of the quantity sensed, digital computing means for processing the output of said electrical circuit means to develop information representing a precipitation condition of the pathway, and display means connected to said digital computing means for displaying the information representing the precipitation condition of the pathway.

18. Apparatus as set forth in claim 14 wherein said sensor means comprises at least one additional conductor embedded in the block and exposed to the precipitation.

19. Apparatus as set forth in claim 14 further comprising means surrounded by said block for capacitively sensing the presence of atmospheric precipitation, means connected to said means for capacitively sensing for producing a first electrical signal indicative of presence of precipitation, means connected to said pair of conductors for supplying a second electrical signal the magnitude of which is a function of the conductance between said pair of conductors, and means for providing an electrical output which indicates an icy surface condition in response to the first electrical signal when the second electrical signal reaches a predetermined ice threshold magnitude.

20. Apparatus for detecting the presence and condition of precipitation on the surface of a pathway, comprising:
a block of electrically insulative material adapted to be embedded in the pathway and having a top surface exposed to precipitation;
sensor means including at least three electrical conductors terminating substantially flush with the top surface of the block with the conductors having exposed portions that are exposed to the precipitation, a first distance separating the exposed portions of two of the electrical conductors and a second distance separating the exposed portions of a particular pair of the electrical conductors wherein the second distance is at least ten times the first distance; and
means connected to the electrical conductors for measuring a first quantity related to electrical conductance between the two electrical conductors that are separated by the first distance and a second quantity related to electrical conductance between the particular pair of conductors that are separated by the second distance which is at least ten times the first distance, and for generating an output signal indicative of precipitation condition as a joint function of the first and second quantities.

21. Apparatus as set forth in claim 20 wherein the three electrical conductors comprise first, second and third electrically conductive pins embedded in the block.

22. Apparatus as set forth in claim 21 wherein the pins have center-to-center spacings and the center-to-center spacing between the second and third pins is at least ten times the center-to-center spacing between the first and second pins, and the three pins lie on substantially the same straight line with the second pin between the first and third pins.

23. Apparatus as set forth in claim 20 wherein said two of the conductors are separated by no more than one millimeter and the particular pair of the conductors are separated by at least ten millimeters.

24. Apparatus as set forth in claim 20 wherein said means for measuring and for generating an output signal includes means for supplying the output signal to represent precipitation depth as a function of the ratio of the conductance of precipitation over the first distance to the conductance of precipitation over the second distance.

25. Apparatus as set forth in claim 20 wherein said means for measuring and for generating an output signal includes electrical circuit means for measuring a quantity related to conductance and electrical switching means for selectively connecting the conductors to the electrical circuit means to measure the conductance of the precipitation over the different first and second distances.

26. Apparatus as set forth in claim 25 wherein said means for measuring and for generating an output signal further includes a digital computer having a memory for storing preestablished information relating depth to a ratio of conductances of the precipitation over the first and second distances respectively, and processor means connected to said electrical circuit means for developing an electrical signal representing the conductance ratio and utilizing the memory to obtain a measured depth of the precipitation.

27. Apparatus as set forth in claim 20 wherein said means for measuring and for generating an output signal includes means connected to said conductors for producing respective first electrical signals as a function of the conductances over the first and second distances and digital computer means for supplying the output signal to represent depth in response to the first electrical signals.

28. Apparatus as set forth in claim 20 wherein the top surface of said block has a well portion for gathering precipitation around at least said two of the electrical conductors and fewer than all of said conductors, the conductors in the well portion terminating substantially flush with the well portion, thereby diminishing the influence of depth of precipitation on the conductance between the conductors in the well portion of the top surface.

29. Apparatus as set forth in claim 20 wherein said means for measuring and for producing an output signal includes balanced differential amplifying means having a pair of inputs connected to the electrical conductors, said balanced differential amplifying means producing an analog electrical output as a function of conductance of the precipitation between the electrical conductors.

30. Apparatus as set forth in claim 20 wherein corrosion forms on the exposed portions of the conductors and endows them with a series capacitance in the presence of precipitation, the apparatus further comprising means for producing a warning when the series capacitance in the presence of precipitation falls below a predetermined capacitance indicative of excessive corrosion.

31. Apparatus for detecting the presence and condition of precipitation on the surface of a pathway, comprising:
a block of electrically insulative material adapted to be embedded in the pathway and having a top surface exposed to precipitation;
sensor means including first, second and third electrical conductors embedded in the block and exposed to the precipitation wherein the top surface of said block is provided with a well for gathering precipitation around the first and second electrical conductors, the first and second conductors terminating in the well and the third conductor terminating outside of the well, the first and second conductors being separated by a first distance which is different from a second distance separating the second and third conductors; and
electrical circuit means connected to said first, second and third electrical conductors for measuring a quantity related to conductance of the precipitation between said electrical conductors over the different first and second distances.

32. Apparatus as set forth in claim 31 further comprising electrical switching means for selectively connecting the conductors to the electrical circuit means.

33. Apparatus as set forth in claim 31 further comprising a digital computer having a memory for storing preestablished information relating precipitation depth to a ratio of conductances of the precipitation over the different first and second distances and processor means connected to said electrical circuit means for developing an electrical signal representing a computed value of the ratio of the conductances and utilizing the memory to obtain a measured depth of the precipitation.

34. Apparatus as set forth in claim 31 further comprising digital computer means for supplying an electrical signal representing depth in response to said electrical circuit means.

35. Apparatus for detecting the presence and condition of precipitation on the surface of a pathway, comprising:
a block of electrically insulative material adapted to be embedded in the pathway and exposed to precipitation; sensor means including at least two electrical conductors affixed to the block and exposed to the precipitation, wherein corrosion forms on the conductors and endows them with a series capacitance in the presence of precipitation; and
means for producing a warning when the series capacitance in the presence of precipitation is less than a predetermined capacitance.

36. Apparatus as set forth in claim 35 wherein said means for producing includes an oscillator, an electrical bridge energized from said oscillator, the bridge connected to a pair of the electrical conductors, detecting means connected to the bridge for detecting whether the bridge is balanced, and means for varying the impedance of part of the bridge until the detecting means detects that the bridge is substantially balanced.

37. Apparatus as set forth in claim 36 wherein the detecting means is connected to said bridge to sense a voltage across said bridge representing a depth of null of said bridge, said impedance having a capacitance value and a resistance value, and said means for varying includes electronic control means connected to the detecting means for determining the capacitance value and the resistance value at which the bridge is most deeply nulled and for producing a further electrical output representative of freezing point of the precipitation as a function of the resistance value at which the bridge is most deeply nulled.

38. Apparatus as set forth in claim 35 wherein said block of electrically insulative material includes a well in the top surface of the block for gathering precipitation around at least two of the electrical conductors.

39. Apparatus as set forth in claim 35 further comprising means surrounded by said block for capacitively sensing the presence of precipitation, and means connected to said means for capacitively sensing for producing an electrical signal indicative of presence of precipitation.

40. In a method of making apparatus for detecting the presence and condition of precipitation on the surface of a pathway, the steps of: molding a block of electrically insulative material around a sensor embedded therein for sensing a physical property of the precipitation which property is also influenced by the depth of the precipitation; and providing the top surface of the block with a well that is generally curved in outline above the sensor for gathering precipitation around the sensor thereby diminishing the influence of precipitation depth on the sensor.

41. A method as set forth in claim 40 further including the step of embedding the block of electrically insulative material in the pathway with the top surface of the block exposed to precipitation.

42. In a method of making apparatus for detecting the presence and condition of precipitation on the surface of a pathway, the steps of:
   filling a mold with a curable material around a pair of electrically conductive pins and curing the material to produce a block of electrically insulative material having a top surface and adapted to be embedded in a pathway and exposed to precipitation; and
   grit-blasting the pins and their surrounding part of the top surface of the block to form a well for gathering precipitation entering said well, the electrically conductive pins thereby having portions thereof exposed to precipitation gathered in said well.

43. A method for detecting the presence and condition of precipitation on the surface of a pathway, comprising the steps of:
   providing a block of electrically insulative material molded around at least three electrical conductors terminating substantially flush with a top surface of the block with the conductors having exposed portions that are exposed to precipitation, a first distance separating the exposed portions of two of the electrical conductors and a second distance separating the exposed portions of a particular pair of the electrical conductors wherein the second distance is at least ten times the first distance;
   electronically measuring a first quantity related to electrical conductance between the two electrical conductors that are separated by the first distance and measuring a second quantity related to electrical conductance between the particular pair of conductors that are separated by the second distance which is at least ten times the first distance; and
   generating an electrical output signal indicative of a condition of the precipitation as a joint function of the first and second quantities.

44. In a method for detecting the presence and condition of precipitation on the surface of a pathway, the steps comprising:
   providing a block of electrically insulative material molded around a sensor including electrical conductors exposed to precipitation, wherein corrosion forms on the conductors and endows them with a series capacitance in the presence of precipitation;
   electronically measuring the series capacitance in the presence of precipitation; and
   producing an electrical signal indicating whether or not the series capacitance in the presence of precipitation is less than a predetermined capacitance indicative of excessive corrosion.

45. In a method for detecting the presence and condition of precipitation on the surface of a pathway, the steps comprising:
   providing an electrical bridge with electrical conductors to sense the precipitation wherein the precipitation has a freezing point which is a function of an electrical conductance of the precipitation when the precipitation is wet and the electrical conductors have a series capacitance in series with the electrical conductance of the precipitation, the bridge including an adjustable impedance having an adjustable capacitance value and an adjustable resistance value, wherein the bridge produces a voltage representing a depth of null of the bridge which depends on the adjustable values;
   sensing the voltage from the bridge representing the depth of null of the bridge;
   adjusting the capacitance value and the resistance value of the impedance of the bridge to determine a particular capacitance value and a particular resistance value at which the null is deepest, the particular capacitance value then determined being related to the series capacitance and the particular resistance value thus determined being related to the conductance of the precipitation;
   producing an electrical output representative of a freezing point of the precipitation as a function of the particular resistance value at which the null is deepest provided the particular resistance value is less than or equal to a first predetermined amount indicative of wet precipitation; and
   further producing an electrical signal representing whether or not the particular capacitance value is abnormally low in value provided the particular resistance value is less than or equal to the first predetermined amount.

* * * * *

UNITED STATES PATENT AND TRADEMARK OFFICE
CERTIFICATE OF CORRECTION

PATENT NO. : 4,897,597

DATED : January 30, 1990

INVENTOR(S) : Miles B. Whitener

It is certified that error appears in the above-identified patent and that said Letters Patent is hereby corrected as shown below:

Column 21, line 22-24, "occurs, and the exponductors having exposed portions thereof exposed to precipitation gathered by the well when precipitation occurs, and", should read ---occurs, and---.

Column 26, line 37, "value then determined", should read ---value thus determined---.

Signed and Sealed this

Thirtieth Day of April, 1991

Attest:

HARRY F. MANBECK, JR.

Attesting Officer     Commissioner of Patents and Trademarks